United States Patent
Nalagatla et al.

(10) Patent No.: US 11,259,804 B2
(45) Date of Patent: Mar. 1, 2022

(54) FRAME FOR SURGICAL STAPLER AND ASSOCIATED METHOD OF MANUFACTURE WITH STAMPING

(71) Applicant: ETHICON LLC, Guaynabo, PR (US)

(72) Inventors: Anil K. Nalagatla, Mason, OH (US); Frederick E. Shelton, IV, Hillsboro, OH (US); Chester O. Baxter, III, Loveland, OH (US); Sohom Bairagi, Kolkata (IN); Yogesh Deshpande, Pune (IN); Sambit Kumar Acharya, Kolkata (IN); Chinmaya Ranjan Dash, Kanchipuram (IN)

(73) Assignee: Cilag GmbH International, Zug (CH)

( * ) Notice: Subject to any disclaimer, the term of this patent is extended or adjusted under 35 U.S.C. 154(b) by 139 days.

(21) Appl. No.: 16/236,703

(22) Filed: Dec. 31, 2018

(65) Prior Publication Data

US 2020/0205815 A1 Jul. 2, 2020

(51) Int. Cl.
*A61B 17/072* (2006.01)
*B21K 5/00* (2006.01)
(Continued)

(52) U.S. Cl.
CPC .......... *A61B 17/072* (2013.01); *A61B 17/068* (2013.01); *B21K 5/00* (2013.01);
(Continued)

(58) Field of Classification Search
CPC ................ A61B 17/068; A61B 17/072; A61B 17/07207; A61B 17/115; A61B 17/1155;
(Continued)

(56) References Cited

U.S. PATENT DOCUMENTS 5,163,945 A 11/1992 Ortiz et al.
5,205,459 A 4/1993 Brinkerhoff et al.
(Continued)

FOREIGN PATENT DOCUMENTS

CN 102 895 010 B 12/2014
CN 106 923 875 A 7/2017
(Continued)

OTHER PUBLICATIONS

U.S. Appl. No. 12/031,573, entitled "Surgical Cutting and Fastening Instrument Having RF Electrodes," filed Feb. 14, 2008.
(Continued)

*Primary Examiner* — Scott A Smith
(74) *Attorney, Agent, or Firm* — Frost Brown Todd LLC

(57) ABSTRACT

A method is used to manufacture a frame of a curved surgical stapler. The method includes manufacturing a first portion of the frame of the curved surgical stapler separate from the first portion. The first portion includes a first curvilinear portion of an end effector and a first alignment feature. The method also includes manufacturing a second portion of the frame of the curved surgical stapler. The second portion includes a second alignment feature. The method also includes manufacturing a third portion of the frame of the curved surgical stapler separate from either of the first or second portions. The third portion includes a C-shaped track. The method also includes aligning the first and second portions portion with the second portion by aligning the first and second alignment features. The method also includes coupling the first and second portions of the frame of the curved surgical stapler together.

20 Claims, 25 Drawing Sheets

(51) Int. Cl.
*A61B 17/068* (2006.01)
*B33Y 10/00* (2015.01)
*A61B 17/00* (2006.01)

(52) U.S. Cl.
CPC ............... *A61B 2017/00477* (2013.01); *A61B 2017/00526* (2013.01); *A61B 2017/07214* (2013.01); *A61B 2017/07221* (2013.01); *A61B 2017/07257* (2013.01); *A61B 2017/07271* (2013.01); *A61B 2017/07285* (2013.01); *B33Y 10/00* (2014.12)

(58) Field of Classification Search
CPC ........... A61B 2017/00398; A61B 2017/00477; A61B 2017/07271; A61B 2017/07278; A61B 2017/07214; A61B 2017/07221; A61B 2017/2945
USPC ...... 227/19, 175.1, 176.1, 180.1; 606/1, 139, 606/205, 219
See application file for complete search history.

(56) References Cited

U.S. PATENT DOCUMENTS

| | | | |
|---|---|---|---|
| 5,271,544 A | | 12/1993 | Fox et al. |
| 5,275,322 A | | 1/1994 | Brinkerhoff et al. |
| 5,285,945 A | | 2/1994 | Brinkerhoff et al. |
| 5,292,053 A | | 3/1994 | Bilotti et al. |
| 5,333,773 A | | 8/1994 | Main et al. |
| 5,342,373 A | | 8/1994 | Stefanchik et al. |
| 5,350,104 A | | 9/1994 | Main et al. |
| 5,403,312 A | | 4/1995 | Yates et al. |
| 5,431,668 A | | 7/1995 | Burbank, III et al. |
| 5,445,167 A | | 8/1995 | Yoon et al. |
| 5,533,661 A | | 7/1996 | Main et al. |
| 5,601,573 A | | 2/1997 | Fogelberg et al. |
| 5,810,240 A | * | 9/1998 | Robertson ............ A61B 17/072 227/175.2 |
| 5,951,574 A | | 9/1999 | Stefanchik et al. |
| 6,805,273 B2 | * | 10/2004 | Bilotti ................ A61B 17/1114 227/180.1 |
| 6,817,508 B1 | * | 11/2004 | Racenet ............... A61B 17/072 227/175.2 |
| 6,988,650 B2 | | 1/2006 | Schwemberger et al. |
| 7,000,818 B2 | | 2/2006 | Shelton, IV et al. |
| 7,134,587 B2 | | 11/2006 | Schwemberger et al. |
| 7,147,139 B2 | | 12/2006 | Schwemberger et al. |
| 7,147,140 B2 | | 12/2006 | Wukusick et al. |
| 7,204,404 B2 | | 4/2007 | Nguyen et al. |
| 7,207,472 B2 | | 4/2007 | Wukusick et al. |
| 7,261,724 B2 | | 8/2007 | Molitor et al. |
| 7,380,696 B2 | | 6/2008 | Shelton, IV et al. |
| 7,407,076 B2 | * | 8/2008 | Racenet ............... A61B 17/072 227/175.1 |
| 7,422,139 B2 | | 9/2008 | Shelton, IV et al. |
| 7,464,849 B2 | | 12/2008 | Shelton, IV et al. |
| 7,670,334 B2 | | 3/2010 | Hueil et al. |
| 7,686,820 B2 | | 3/2010 | Huitema et al. |
| 7,699,860 B2 | | 4/2010 | Huitema et al. |
| 7,731,724 B2 | | 6/2010 | Huitema et al. |
| 7,753,245 B2 | | 7/2010 | Boudreaux et al. |
| 7,845,537 B2 | | 12/2010 | Shelton, IV et al. |
| 7,980,443 B2 | | 7/2011 | Scheib et al. |
| 8,029,520 B2 | * | 10/2011 | Korvick ............. A61B 17/0293 606/153 |
| 8,038,686 B2 | | 10/2011 | Huitema et al. |
| 8,210,411 B2 | | 7/2012 | Yates et al. |
| 8,220,688 B2 | | 7/2012 | Laurent et al. |
| 8,262,679 B2 | | 9/2012 | Nguyen |
| 8,308,040 B2 | | 11/2012 | Huang et al. |
| 8,393,514 B2 | | 3/2013 | Shelton, IV et al. |
| 8,408,439 B2 | | 4/2013 | Huang et al. |
| 8,453,914 B2 | | 6/2013 | Laurent et al. |
| 8,561,870 B2 | | 10/2013 | Baxter, III et al. |
| 8,608,045 B2 | | 12/2013 | Smith et al. |
| 8,733,613 B2 | | 5/2014 | Huitema et al. |
| 8,910,847 B2 | | 12/2014 | Nalagatla et al. |
| 9,072,535 B2 | | 7/2015 | Shelton, IV et al. |
| 9,101,358 B2 | | 8/2015 | Kerr et al. |
| 9,125,651 B2 | * | 9/2015 | Mandakolathur Vasudevan ......... A61B 17/072 |
| 9,186,142 B2 | | 11/2015 | Fanelli et al. |
| 9,345,481 B2 | | 5/2016 | Hall et al. |
| 9,517,065 B2 | | 12/2016 | Simms et al. |
| 9,713,469 B2 | | 7/2017 | Leimbach et al. |
| 9,717,497 B2 | | 8/2017 | Zerkle et al. |
| 9,795,379 B2 | | 10/2017 | Leimbach et al. |
| 9,808,248 B2 | | 11/2017 | Hoffman |
| 9,839,421 B2 | | 12/2017 | Zerkle et al. |
| 9,867,615 B2 | | 1/2018 | Fanelli et al. |
| 9,907,552 B2 | | 3/2018 | Measamer et al. |
| 9,936,949 B2 | | 4/2018 | Measamer et al. |
| 10,092,292 B2 | | 10/2018 | Boudreaux et al. |
| 2005/0139636 A1 | | 6/2005 | Schwemberger et al. |
| 2005/0143759 A1 | | 6/2005 | Kelly |
| 2005/0145672 A1 | | 7/2005 | Schwemberger et al. |
| 2005/0145673 A1 | * | 7/2005 | Nguyen ............... A61B 17/072 227/176.1 |
| 2007/0175955 A1 | | 8/2007 | Shelton, IV et al. |
| 2014/0239037 A1 | | 8/2014 | Boudreaux et al. |
| 2014/0263552 A1 | | 9/2014 | Hall et al. |
| 2015/0083772 A1 | | 3/2015 | Miller et al. |
| 2015/0083773 A1 | | 3/2015 | Measamer et al. |
| 2015/0083774 A1 | | 3/2015 | Measamer et al. |
| 2015/0083775 A1 | | 3/2015 | Leimbach et al. |
| 2016/0249914 A1 | * | 9/2016 | Zhang ................. A61B 17/295 227/175.3 |
| 2016/0256159 A1 | * | 9/2016 | Pinjala ............. A61B 17/07207 |
| 2016/0270783 A1 | * | 9/2016 | Yigit ................ A61B 17/07207 |
| 2016/0374672 A1 | | 12/2016 | Bear et al. |
| 2017/0014134 A1 | * | 1/2017 | Chen ................... A61B 17/072 |
| 2017/0027571 A1 | | 2/2017 | Nalagatla et al. |
| 2017/0027574 A1 | * | 2/2017 | Nalagatla ............. A61B 17/068 |
| 2017/0189024 A1 | * | 7/2017 | Adams ................ A61B 17/072 |
| 2017/0258471 A1 | | 9/2017 | DiNardo et al. |
| 2018/0132849 A1 | | 5/2018 | Miller et al. |
| 2018/0132853 A1 | | 5/2018 | Miller et al. |
| 2018/0153544 A1 | * | 6/2018 | Maddur Shankarsetty ................. A61B 17/072 |
| 2018/0310938 A1 | | 11/2018 | Kluener et al. |
| 2018/0310939 A1 | | 11/2018 | Stager et al. |

FOREIGN PATENT DOCUMENTS

| | | |
|---|---|---|
| WO | WO 01/91646 A1 | 12/2001 |
| WO | WO 2014/043971 A1 | 3/2014 |

OTHER PUBLICATIONS

European Search Report, Extended, and Written Opinion dated Aug. 3, 2020 for Application No. EP 19220103.6, 18 pgs.
International Search Report and Written Opinion dated Jun. 23, 2020 for Application No. PCT/IB2019/061247, 20 pgs.

* cited by examiner

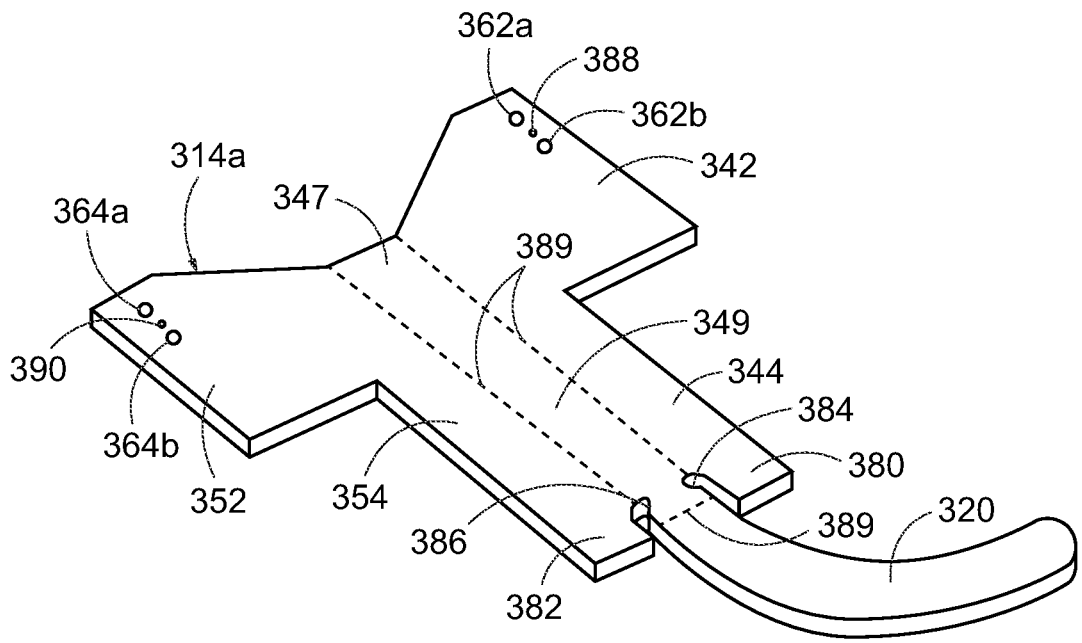
FIG. 10A
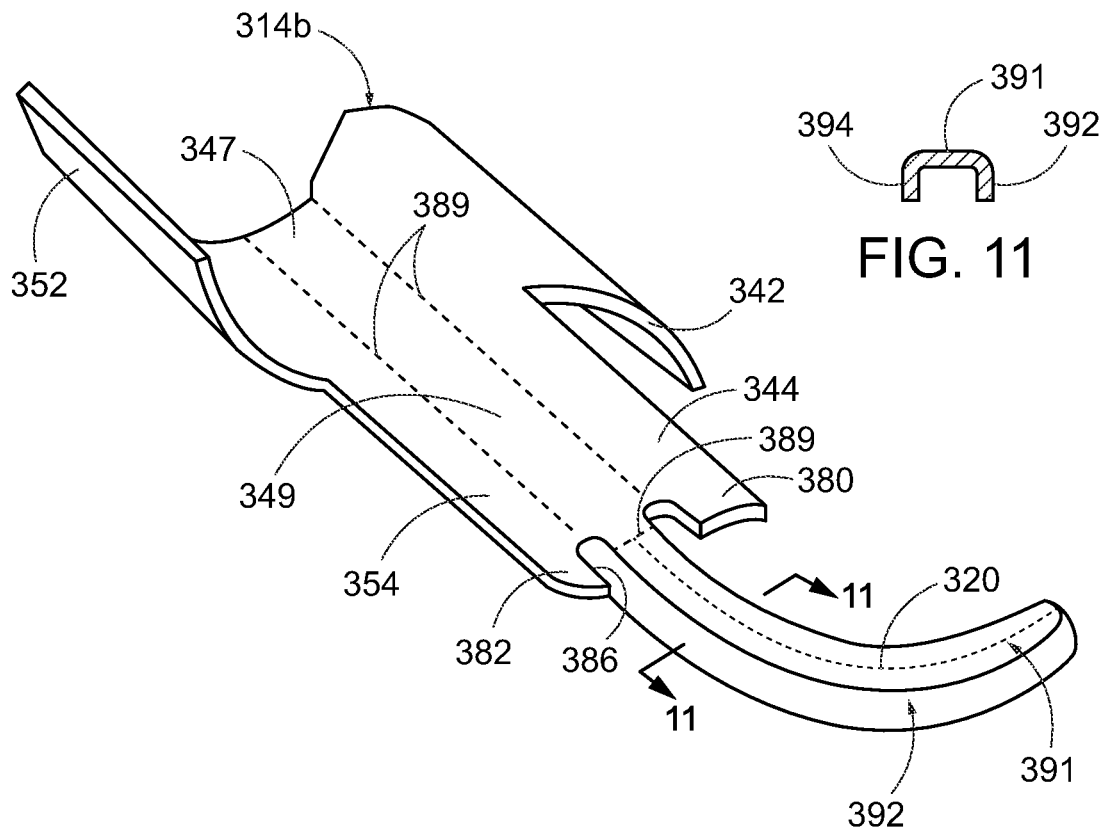
FIG. 11
FIG. 10B

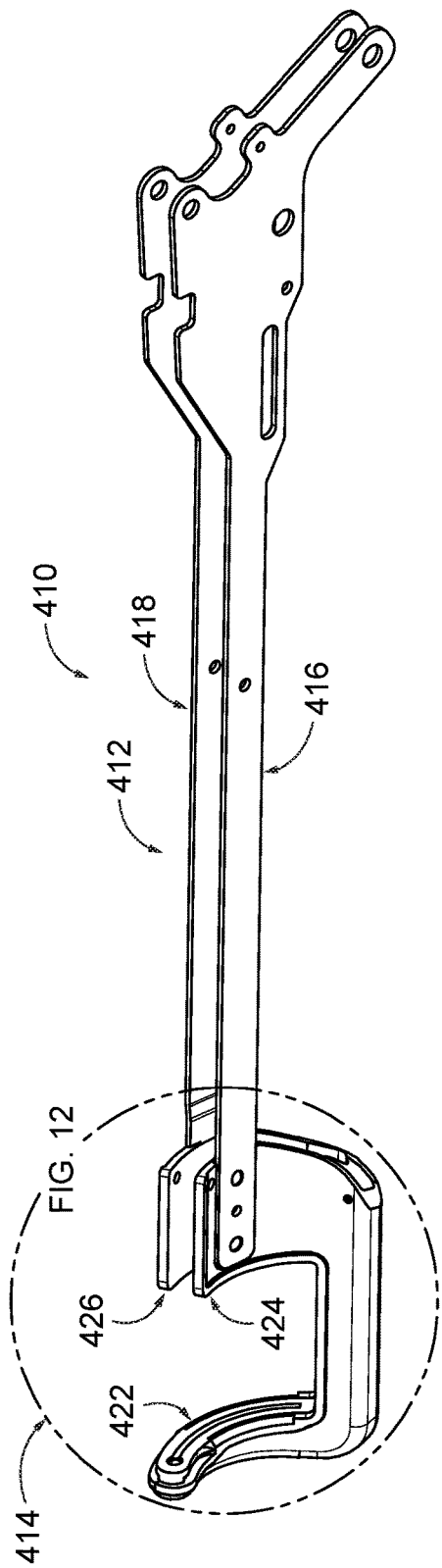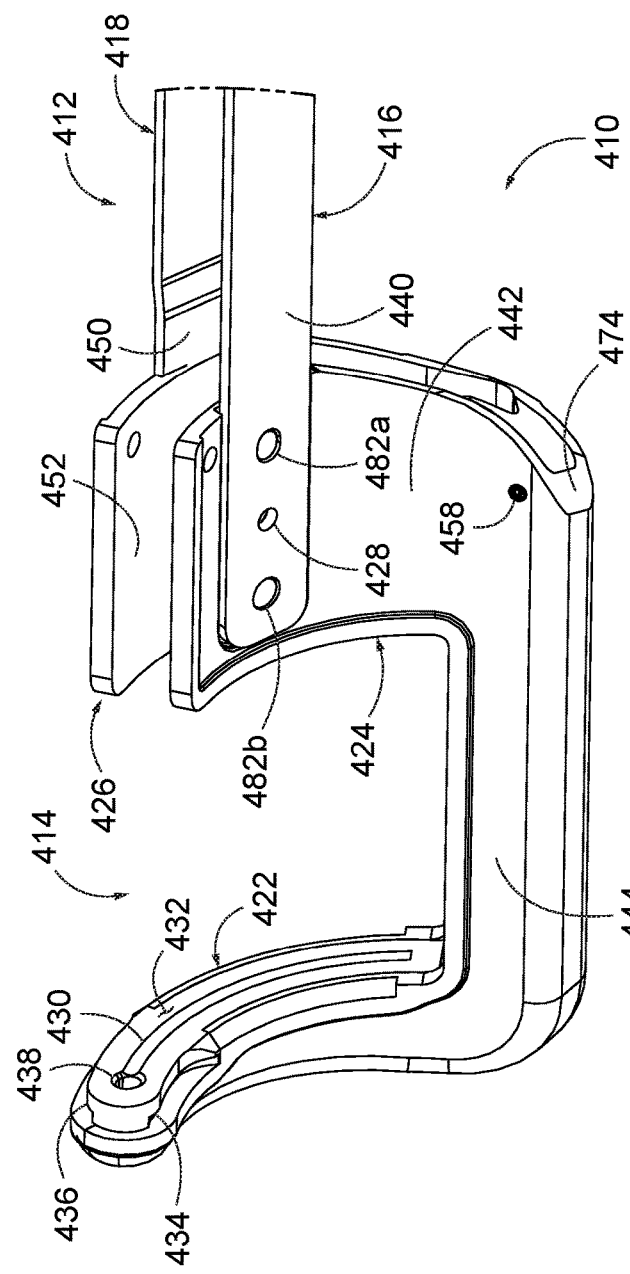

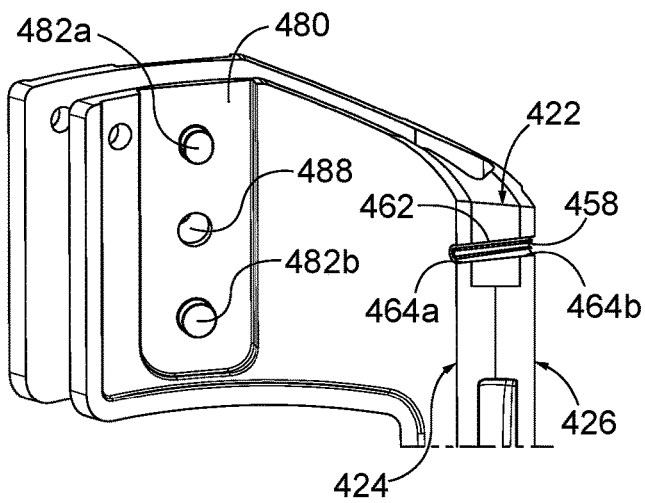
FIG. 17
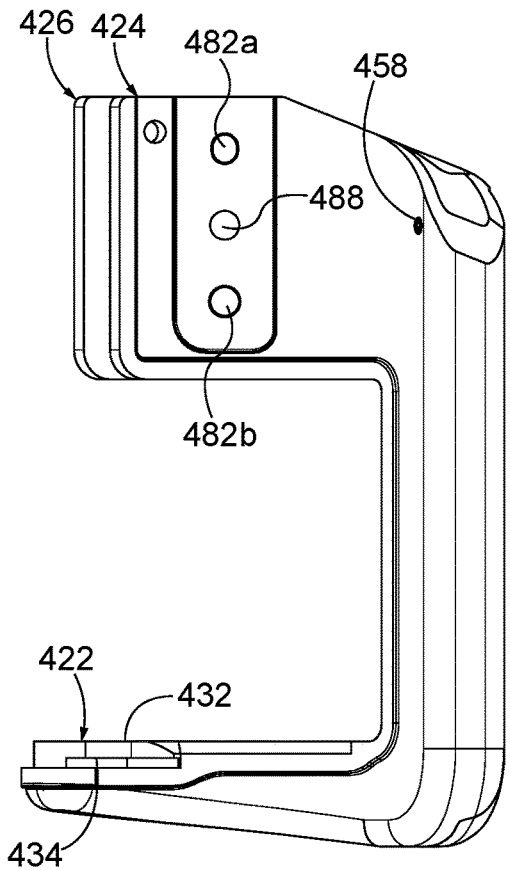 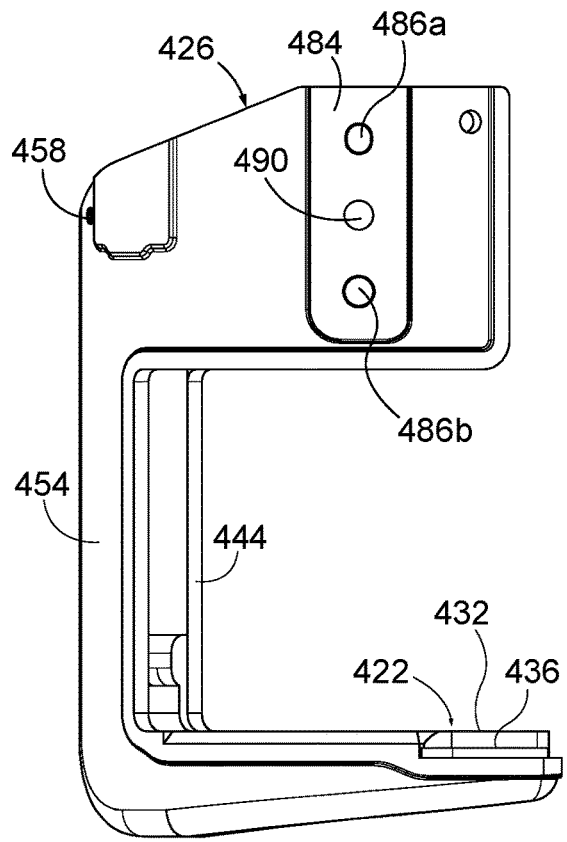
FIG. 18     FIG. 19

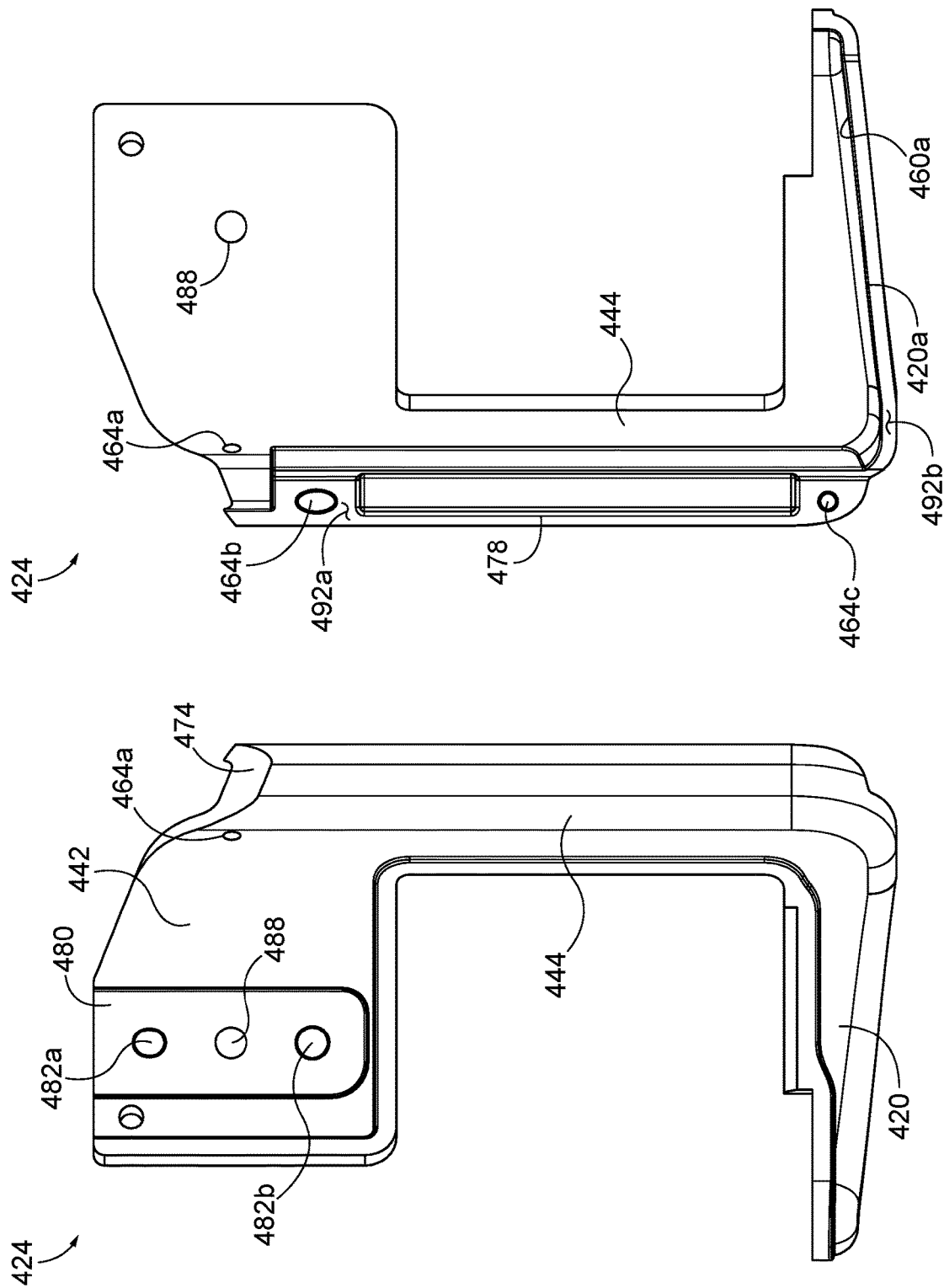

FRAME FOR SURGICAL STAPLER AND ASSOCIATED METHOD OF MANUFACTURE WITH STAMPING

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10A depicts a perspective view of a distal portion of a second exemplary frame that may be incorporated into the surgical stapling instrument of FIG. 1 prior to being bent;

FIG. 10B depicts a perspective view of the distal portion of the frame of FIG. 10A after being bent;

FIG. 11 depicts a sectional view of a distal anvil support portion of the distal portion of the frame of FIG. 10B taken along line 11-11 of FIG. 10B;

FIG. 12 depicts right rear perspective view of a third exemplary frame that may be incorporated into the surgical stapling instrument of FIG. 1;

FIG. 13 depicts an enlarged right rear perspective view of a distal portion of the frame of FIG. 12;

FIG. 17 depicts an enlarged top right sectional view of the end effector frame of FIG. 15, with the fastener extending through the end effector frame;

FIG. 18 depicts a right plan view of the end effector frame of FIG. 12;

FIG. 19 depicts a left plan view of the end effector frame of FIG. 12;

FIG. 21 depicts a right plan view of the left end effector frame portion of FIG. 20;

FIG. 22 depicts a left plan view of the left end effector frame portion of FIG. 20;

Figure 1A:
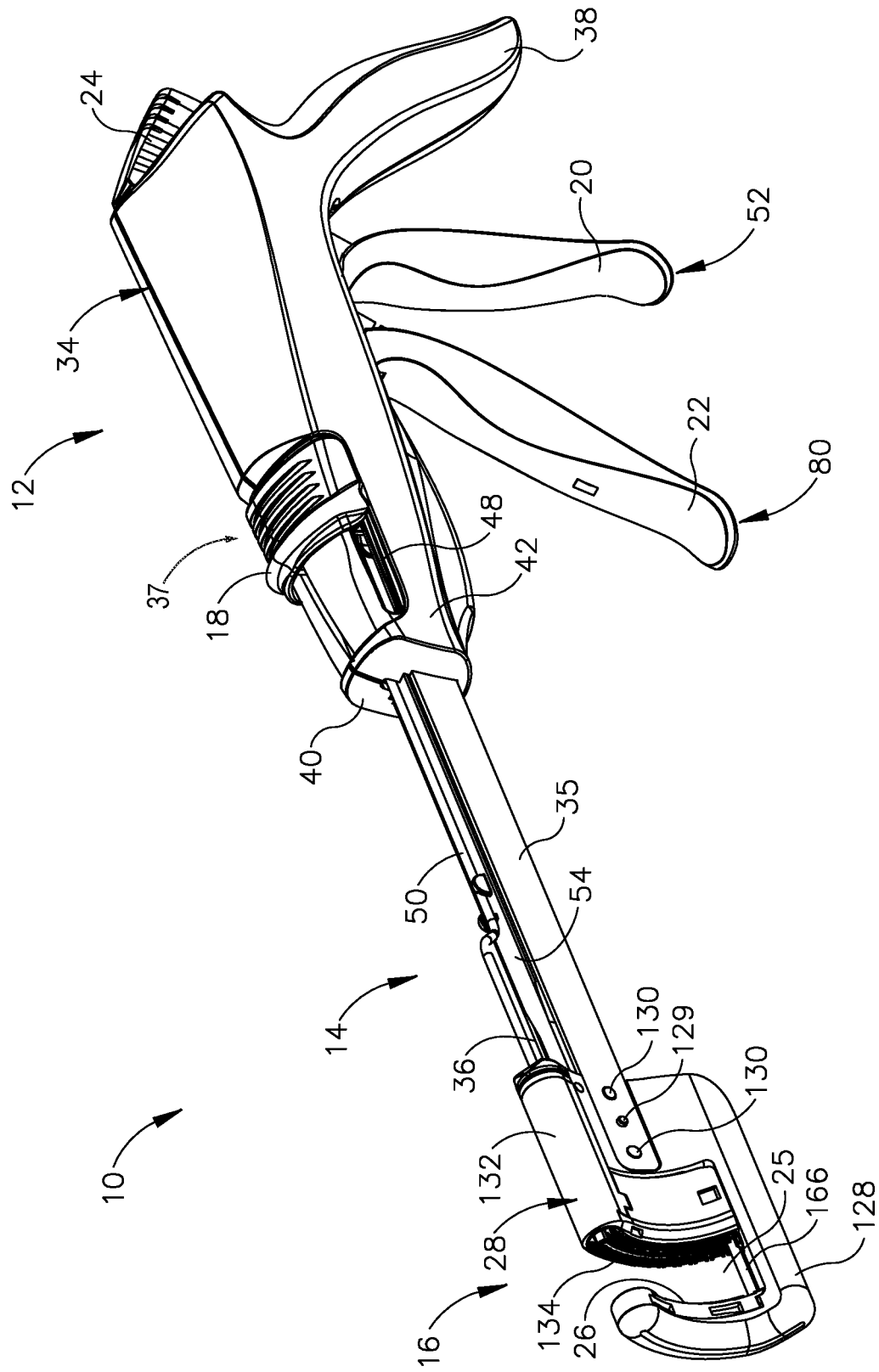
FIG. 1A depicts a right front perspective view of an exemplary surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

I. Exemplary Surgical Stapler

FIG. 1A depicts an exemplary surgical stapling and severing instrument (10) that includes a handle assembly (12), a shaft assembly (14), and an end effector (16) distally projecting from shaft assembly (14). It should be understood that terms such as "proximal," "distal," "right," and "left" are used herein with reference to a clinician gripping handle assembly (12) of surgical stapling instrument (10). Thus, end effector (16) is distal with respect to the relatively proximal handle assembly (14). Except as otherwise described herein, instrument (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; and/or U.S. Pat. Pub. No. 2017/0027571, entitled "Surgical Instrument Comprising Systems for Assuring the Proper Sequential Operation of the Surgical Instrument," published on Feb. 2, 2017, issued as U.S. Pat. No. 10,194,913 on Feb. 5, 2019, the disclosure of which is incorporated by reference herein.

Figure 1B:
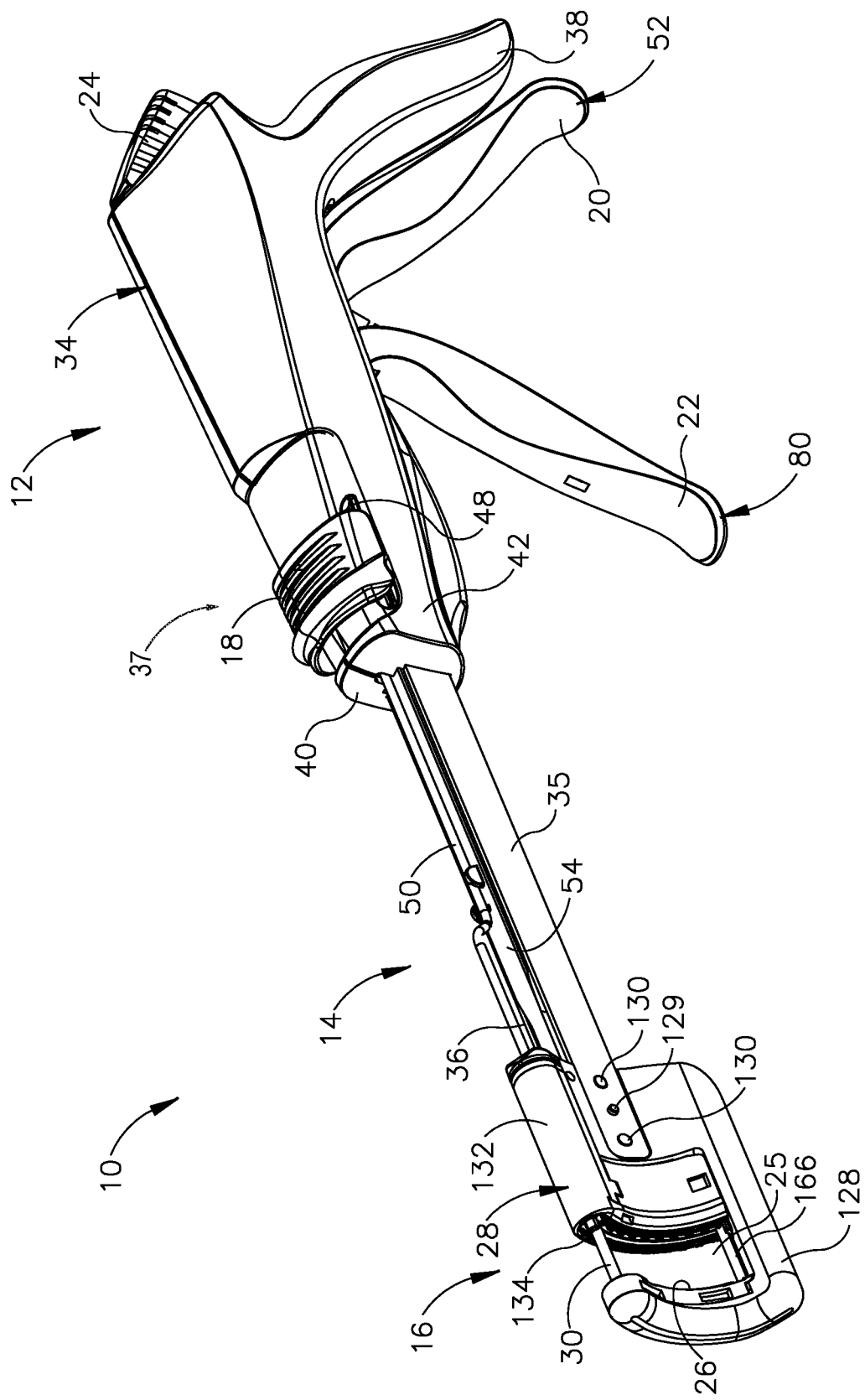
FIG. 1B depicts a right front perspective view of the surgical stapling instrument of FIG. 1A with the pin actuation mechanism in a closed position and the staple cartridge in the open position.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). As shown in FIG. 1A, slide (18) and closure trigger (20) are in open configurations, such that end effector (16) is configured to receive tissue laterally within a gap (25) between an anvil (26) and a cartridge (28)

of end effector (16). Translating slide (18) distally toward end effector (16) slides a retaining pin (30) of end effector distally as shown in FIG. 1B for capturing the tissue between anvil (26) and cartridge (28). With respect to FIGS. 1C and 1D, sequentially actuating closure trigger (20) and firing trigger (22) respectively compresses the tissue between anvil (26) and cartridge (28) in a closed configuration and then forms a plurality of staples (not shown) within the tissue and severs the tissue with a knife (not shown) for treatment. Additional details regarding these exemplary actuation mechanisms will be provided below in greater detail.

A. Exemplary Handle Assembly and Shaft Assembly

As shown in FIG. 1A, handle assembly (12) has a handle housing (34), a pair of handle frame plates (35, 36) within handle housing (34) extending along shaft assembly (14), saddle shaped slide (18), closure trigger (20), and firing trigger (22) as briefly discussed above. Handle housing (34) defines a hand grip (38), which the operator, such as a surgeon, grasps with the palm of at least one hand. Handle housing (34) is formed by a right shroud handle portion (40) and a left shroud handle portion (42). Closure trigger (20) is proximally positioned relative to firing trigger (22) and each are pivotally mounted to frame plates (35, 36) to extend underneath a remainder of handle assembly (12) for manipulation by the fingers of the operator. Closure and firing triggers (20, 22) are shown in unactuated positions prior to closing end effector (16) and firing staples (not shown) and/or knife. Consequently, cartridge (28) is spaced from anvil (26) for receiving tissue within gap (25) therebetween.

Surgical stapling instrument (10) captures tissue via a tissue retaining pin actuation mechanism (37) prior to actuation of the closure and firing triggers (20, 22). Retaining pin actuation mechanism (37) is mounted on an upper surface of handle housing (34) and is configured to linearly translate between proximal and distal positions. Slide (18) slides along slots (48) (see FIG. 1A). A distal end of a push rod (50) connects to retaining pin (30) (see FIG. 1B) such that distal movement of slide (18) causes push rod (50) to similarly slide proximally along shaft assembly (14) for moving retaining pin (30) to the closed configuration, which will be discussed below in greater detail.

Figure 2:
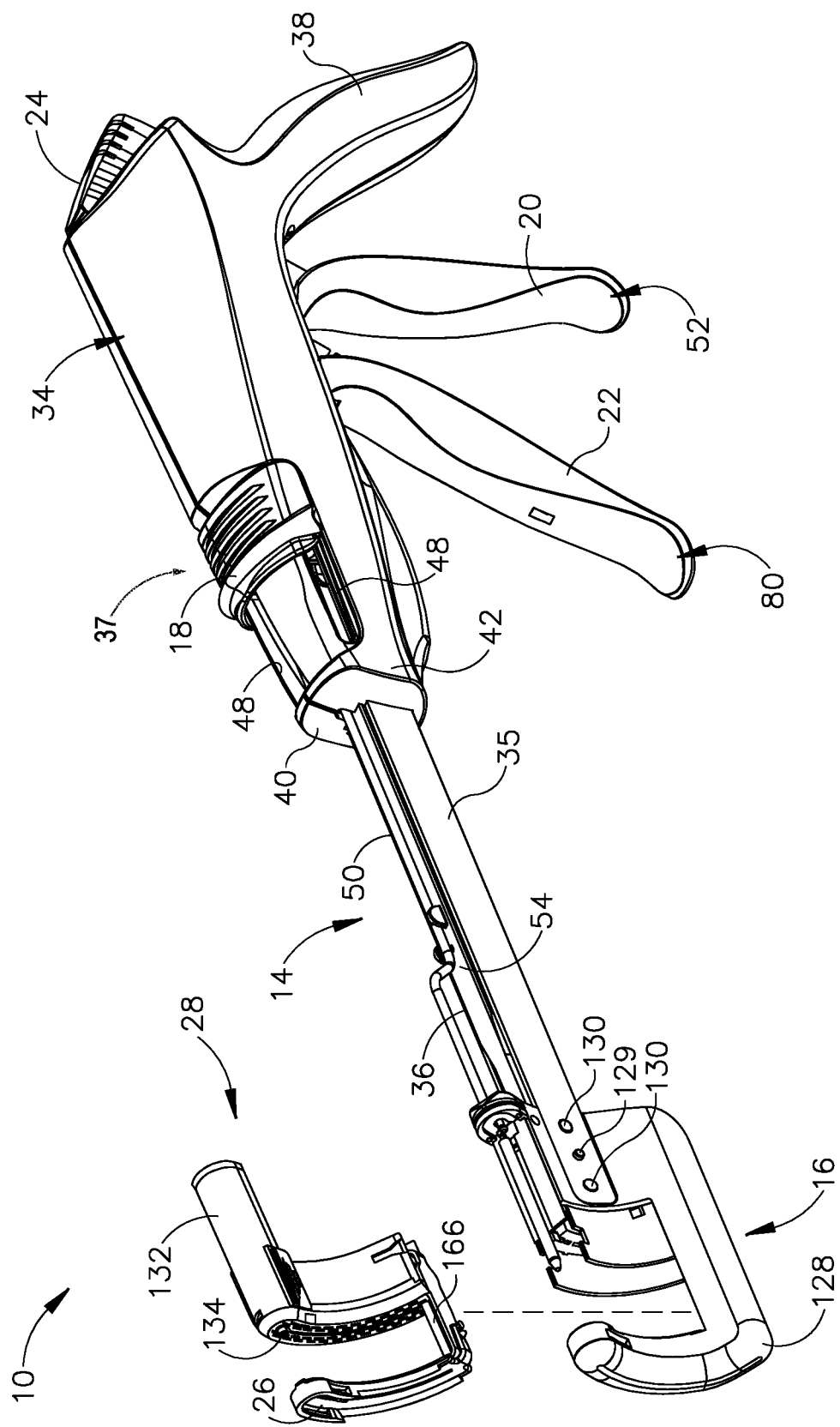
FIG. 2 depicts a partially exploded right front perspective view of the surgical stapling instrument of FIG. 1A showing the staple cartridge removed from a remainder of an end effector.

A closure mechanism (52), which includes closure trigger (20), is configured to selectively move cartridge (28) toward the tissue positioned between anvil (26) and cartridge (28) in the closed configuration in anticipation of stapling and/or cutting the tissue. Closure mechanism (52) further includes an elongated closure member (54), with a generally U-shaped cross-section, extending distally from handle assembly (12), through shaft assembly (14), and into end effector (16) for receiving a cartridge (28) (see FIG. 2) at a distal end portion thereof as discussed below. A proximal end portion of closure member (54) is operatively connected to closure trigger (20) by a plurality of linkages configured to convert pivoting motion of closure trigger (20) into translation of closure member (54). More particularly, the intermediate and proximal end portions of closure member (54) extend through handle assembly (12) between left and right handle frame plates (35, 36). Closure trigger (20) descends from the slotted closure arm link (62) both toward and away from hand grip (38). Closure member (54) is further configured for directing movement of tissue retaining pin actuation mechanism (37) to automatically direct movement of retaining pin (30) to the closed configuration while the operator squeezes closure trigger (20). Such automation may be useful in the event that the operator did not manually move slide (18) to the distal position before actuating trigger (20). Slide (18) is thereby dragged along handle housing (34) from the proximal position to the distal position in the event that the operator did not manually manipulate slide (18) to the distal position before actuating trigger (20).

Figure 1C:
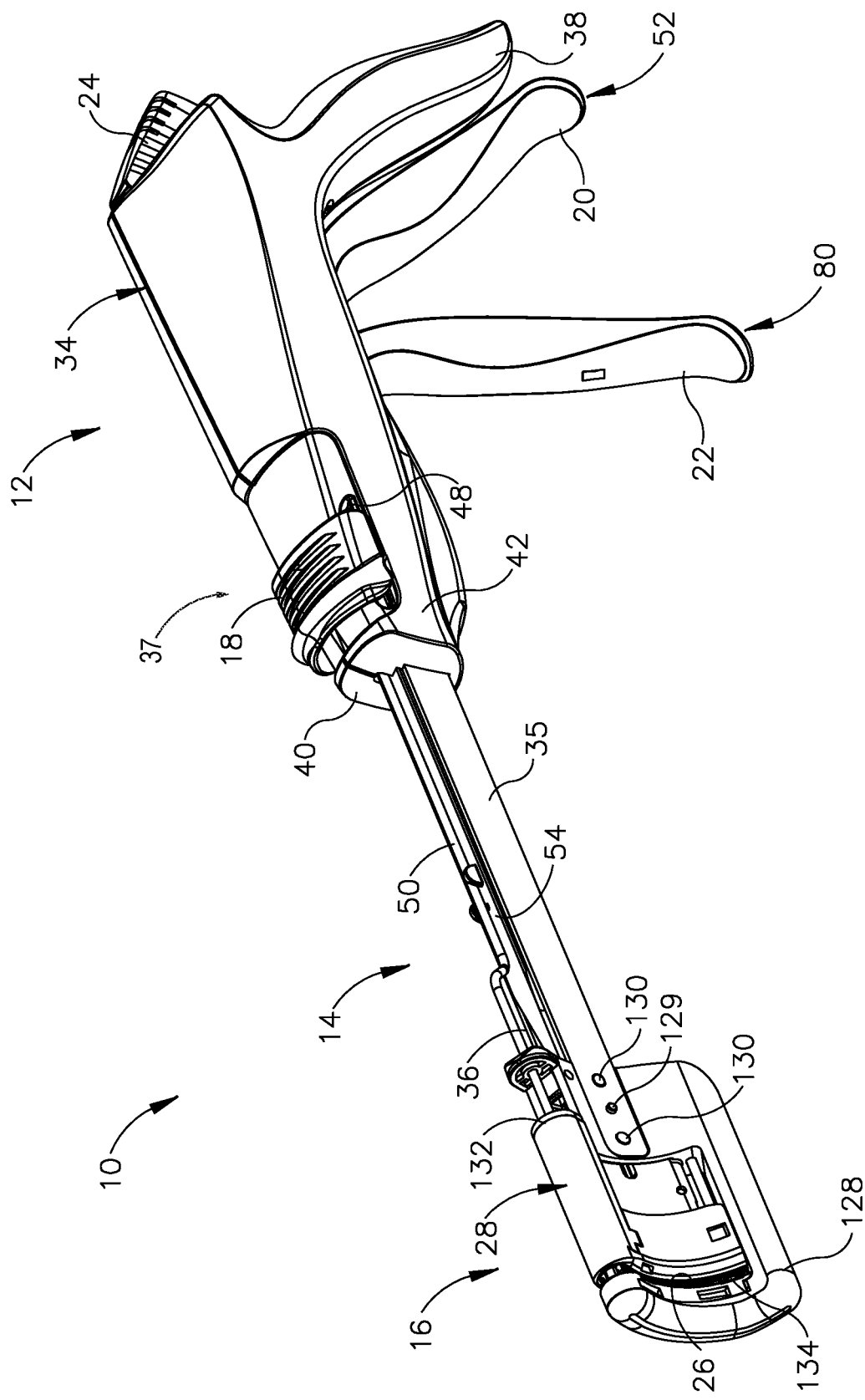
FIG. 1C depicts a right front perspective view of the surgical stapling instrument of FIG. 1A with the pin actuation mechanism in the closed position and the staple cartridge in a closed position via actuation of a closure mechanism.
Figure 1D:
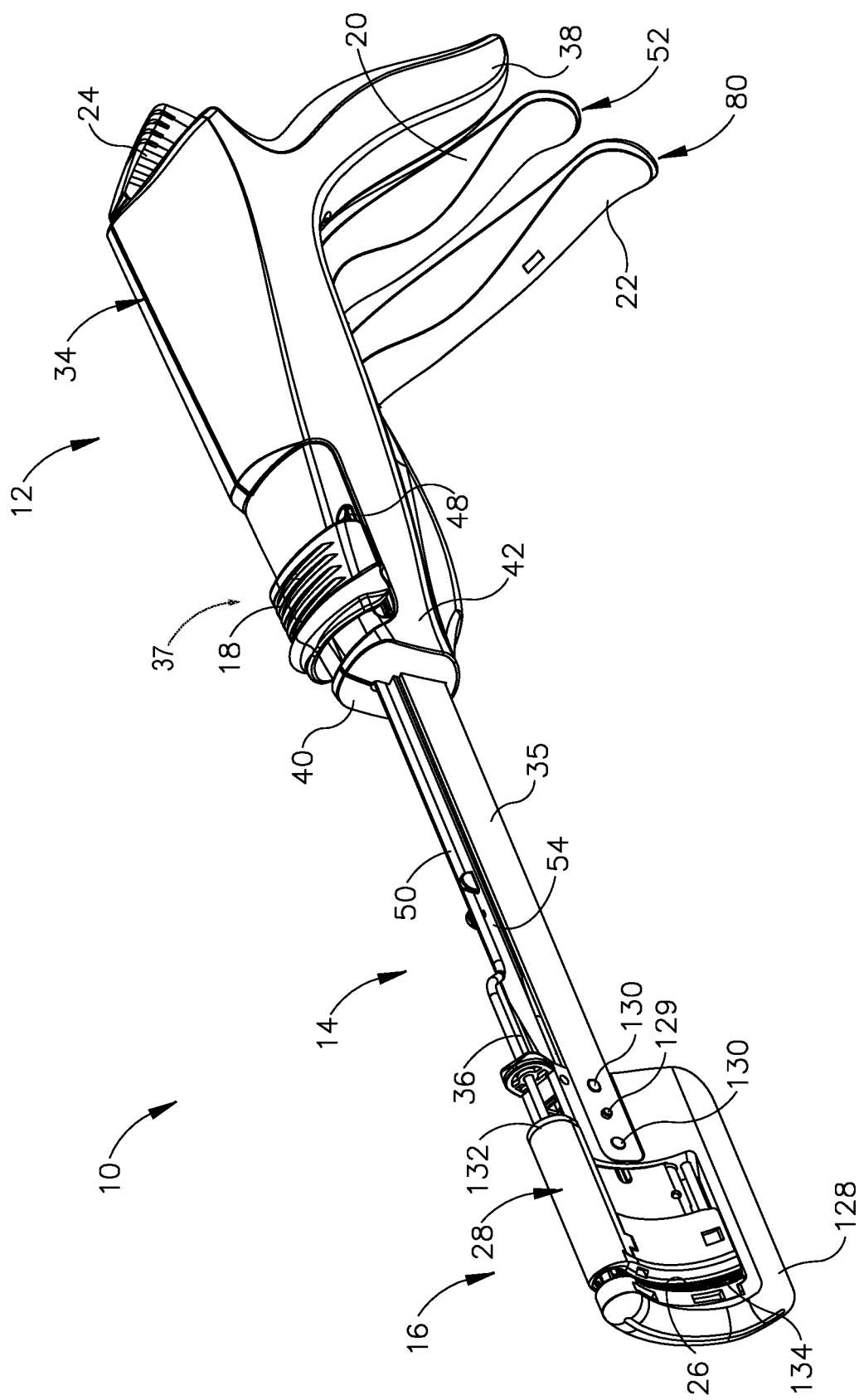
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.

The operator further squeezes the closure trigger (20) to hand grip (38) as shown in FIG. 1C to effectively set surgical stapling instrument (10) in the closed configuration prior to forming the staples (not shown) and severing the tissue as discussed briefly above. Exemplary handle assembly (12) is configured to form the staples (not shown) and sever the tissue via a firing mechanism (80) upon operator manipulation of firing trigger (22) toward closure trigger (20) as shown in FIG. 1D. With respect to FIGS. 1C-1D, firing mechanism (80), which includes firing trigger (22), extends distally from handle assembly (12) and within end effector (16).

Upon operator release of one or both of closure and firing triggers (20, 22) while one or both of triggers (20, 22) is/are in a fired position, or in an intermediate position between the unactuated and fired positions, surgical stapling instrument (10) may be further configured to releasably lock in one of a variety of configurations. The operator may then release hand grip (38) to free one or more hands for another task during the surgical procedure and, when desired, release surgical stapling instrument (10) from its locked position by release button (24).

Surgical stapling instrument (10) of the present example includes each of handle frame plates (35, 36), push rod (50), closure member (54), and firing bar extending continuously from handle assembly (12) to end effector (16), thereby defining shaft assembly (14) extending therebetween. Handle frame plates (35, 36), push rod (50), closure member (54), and a firing bar of surgical stapling instrument (10) provide merely a subset of elongated components extending distally from handle assembly (12) as shaft assembly (14). Alternatively, shaft assembly (14) may include additional components, such as an articulating joint, or may include a rearrangement of various components such that shaft assembly (14) may be modular relative to handle assembly (12). In any case, it will be appreciated that the invention is not intended to be limited to shaft assembly (14) described herein, and may include various alternative arrangements for operatively connecting end effector (16) to handle assembly (12). Of course, handle assembly (12) and shaft assembly (14) may have a variety of other components, features, and operabilities, in addition to or in lieu of any of those noted above. Other suitable configurations for handle and shaft assemblies (12, 14) will be apparent to those of ordinary skill in the art in view of the teachings herein.

B. Exemplary End Effector

End effector (16) includes anvil (26), replaceable cartridge (28) including a plurality of staples (not shown) and knife (not shown), and retainer pin (30). While end effector (16) of the present example is adapted for use in conjunction with replaceable cartridge (28) having various components, it will be appreciated that the concepts underlying the present invention could be applied to a variety of end effector and cartridge constructions for treating the patient.

End effector (16) provides a surgical fastening assembly that includes cartridge (28) received within a C-shaped supporting structure (128). The term C-shaped is used throughout the specification to describe the concave nature of supporting structure (128) and cartridge (28), The C-shaped construction facilitates enhanced functionality and access to tissue within the patient. The term "C-shaped" as used herein should be construed to include a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure. Supporting structure (128) of end effector (16) is respectively attached to handle frame plates (35, 36) of shaft assembly (14) by a shoulder rivet (129) and posts (130) which extend from supporting structure (128) into receiving holes in handle frame plates (35, 36). The distal end of closure member (54) is disposed to receive cartridge (28) thereon for directing cartridge (28) to the closed configuration.

Cartridge (28) includes anvil (26) coupled to a cartridge housing (132). Cartridge (28) also includes retaining pin (30) and a tissue contacting surface (34). Staples (not shown) are fired from cartridge housing (132) against a staple-forming surface of anvil (26) that faces tissue-contacting surface (134) of cartridge housing (132). Cartridge (28) may also include a removable retainer (not shown) for storage between anvil (26) and tissue contacting surface (34) prior to and/or after use in order to inhibit unintended contact with various portions of cartridge (28).

C. Exemplary Actuation of Cartridge

In the present example, cartridge (28) is driven toward anvil (26) via closure member (54) until reaching the closed configuration with tissue positioned between cartridge (28) and anvil (26) as discussed above with respect to handle assembly (12). While actuation of cartridge (28) includes stapling and severing tissue in this example, it will be appreciated that one or more of these steps may be omitted from treatment as desired by the operator. Moreover, it will be appreciated that surgical stapling instrument (10) may be reconfigured to perform these steps simultaneously or sequentially as desired. It should therefore be understood that the invention is not intended to be limited to the particular operation of surgical stapling instrument (10) or the associated treatment.

As shown in FIG. 1A, cartridge (28) is spaced proximally from anvil (26) to receive tissue within gap (25) in the open configuration. With tissue received between cartridge (28) and anvil (26), the operator manually directs push rod (50) distally via slide (18). Thus, distally translating push rod (50) similarly translates retaining pin (30) to extend from cartridge (28) to anvil (26) and capture tissue between retaining pin (30) and guide pin (166).

As shown in FIG. 1C, manipulation of closure trigger (20) forces closure member (54) to translate distally relative to supporting structure (128) of end effector (16). Closure member (54) supports cartridge (28) thereon such that distal translation of closure member (54) similarly moves firing bar and cartridge (28) toward anvil (26). With cartridge (28) in the closed configuration and the tissue effectively captured in the end effector (16), the operator manipulates firing trigger (22) (see FIG. 1D) toward anvil (26) to the fired position. Once fired, the operator may depress release button (24) and withdraw closure member (54) and firing bar proximally from the actuated, fired position to the unactuated position. At approximately the same time, as cartridge (28) translates proximally with closure member (54), and cartridge housing (132) is held in position. Cartridge (28) may then be removed from supporting structure (128) of end effector (16), discarded, and replaced for further treatment if so desired. Of course, various suitable settings and procedures in which surgical stapling instrument (10) may be used will be apparent to those of ordinary skill in the art in view of the teachings herein.

II. Exemplary Frames and Methods of Manufacture

In some conventional manufacturing processes, an end effector frame (e.g. one that includes supporting structure (128)) of instrument (10) may be machined from a single solid block of material (e.g. metal). As a result, this machining of supporting structure (128) may be time consuming and expensive, both of which are undesirable. As a result, it is desirable to manufacture the frame using a faster, more efficient, and more cost-effective process or system of processes. Conventional machining techniques, being reductive in nature, may also be considered as being inefficient since they may create waste in the material that is removed from the single solid block of material. Additionally, it may be desirable that specific portions and features of supporting structure (128) have tighter tolerances to enhance the performance of instrument (10), while other specific portions and features of supporting structure (128) may have looser tolerances where the precise dimensions are of lesser significance. For example, tighter tolerances may be preferred for surfaces that aid in the coupling of staple cartridge (28) with the end effector (16) and surfaces that aid in the coupling of handle frame plates (35, 36) with the end effector frame of instrument (10). As such, it is desirable to manufacture a frame (210, 310, 410, 510) efficiently, cost effectively, and robustly. Various exemplary alternative frames (210, 310, 410, 510) and associated manufacturing techniques will be described in greater detail below.

A. First Exemplary Frame

Figure 3:
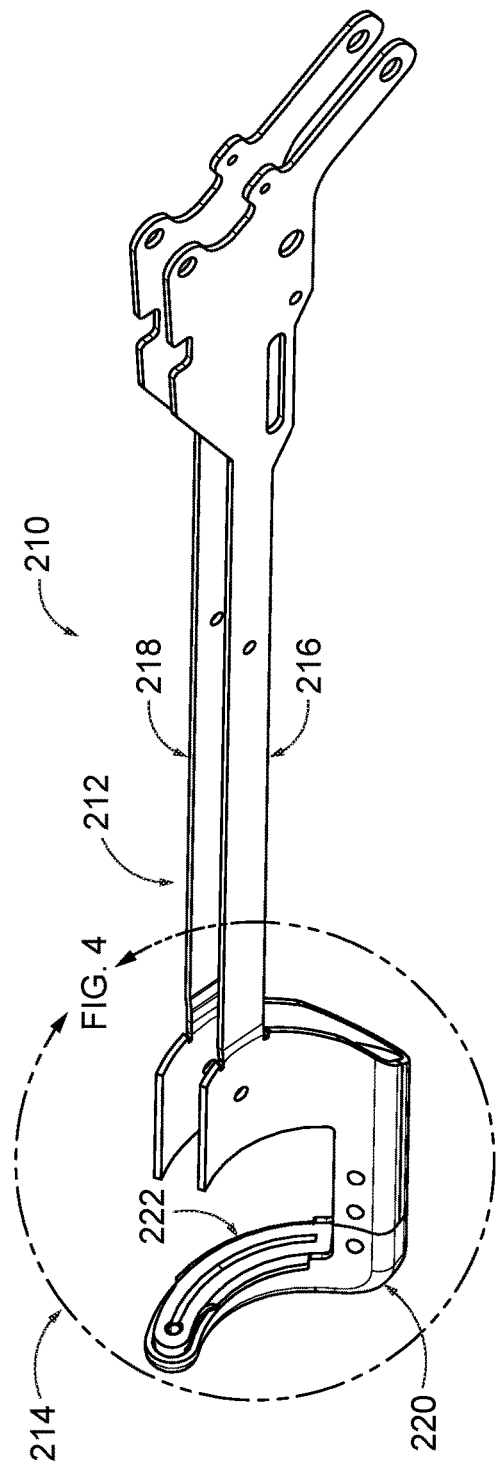
FIG. 3 depicts a right rear perspective view of a first exemplary frame that may be incorporated into the surgical stapling instrument of FIG. 1.

FIGS. 3-9 show a first exemplary frame (210) that may be incorporated into surgical stapling instrument (10) of FIG. 1. FIG. 3 shows frame (210) as including a shaft frame (212) and an end effector frame (214) extending distally from shaft frame (212). Shaft frame (212) includes first and second shaft frame portions, shown as left and right handle frames (216, 218). End effector frame (214) includes a distal anvil support portion (220), an insert (222), and left and right support plates (224, 226) (see FIG. 5). As shown, left and right handle frames (216, 218), distal anvil support portion (220), insert (222), and left and right support plates (224, 226) are each integrally formed as a unitary piece and subsequently coupled together as discussed in greater detailed below. This prevents end effector frame (214) from being machined from a single solid block of material, which as discussed above may be time consuming and expensive.

Figure 4:
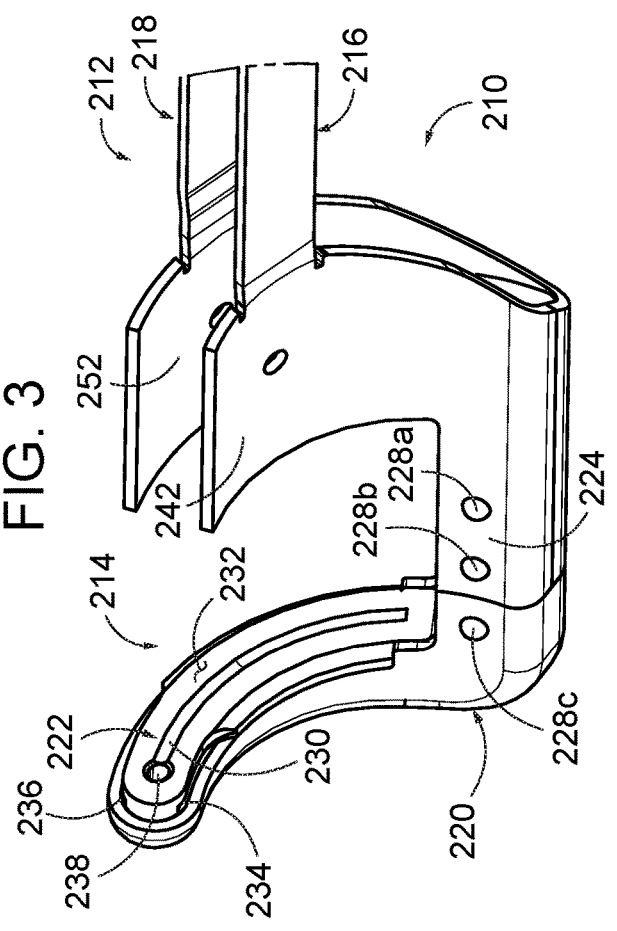
FIG. 4 depicts an enlarged right rear perspective view of a distal portion of the frame of FIG. 3.

FIG. 4 shows an enlarged perspective view of the distal portion of frame (210) of FIG. 3 showing the coupling of shaft frame (212) and end effector frame (214) using fasteners (228a-c), as will be described in greater detail with reference to FIGS. 6-9. Insert (222) includes a C-shaped track (230) disposed within an upper surface (232), with left and right flanges (234, 236) disposed laterally of upper surface (232). C-shaped track (230) includes an enlarged portion (238) configured to receive a distal portion of retaining pin (30) shown in FIGS. 1A-1D. C-shaped track (230) along with a slot of staple cartridge (28) are configured to receive a knife (not shown) therethrough to sever tissue. Insert (222) is configured to receive staple cartridge (28). Insert (222) may be formed for a metallic or polymeric material. More specifically, left and right flanges (234, 236) of insert (222) are configured to slidably receive corresponding portions of staple cartridge (28) as shown in FIGS. 1A-1D.

Figure 5:
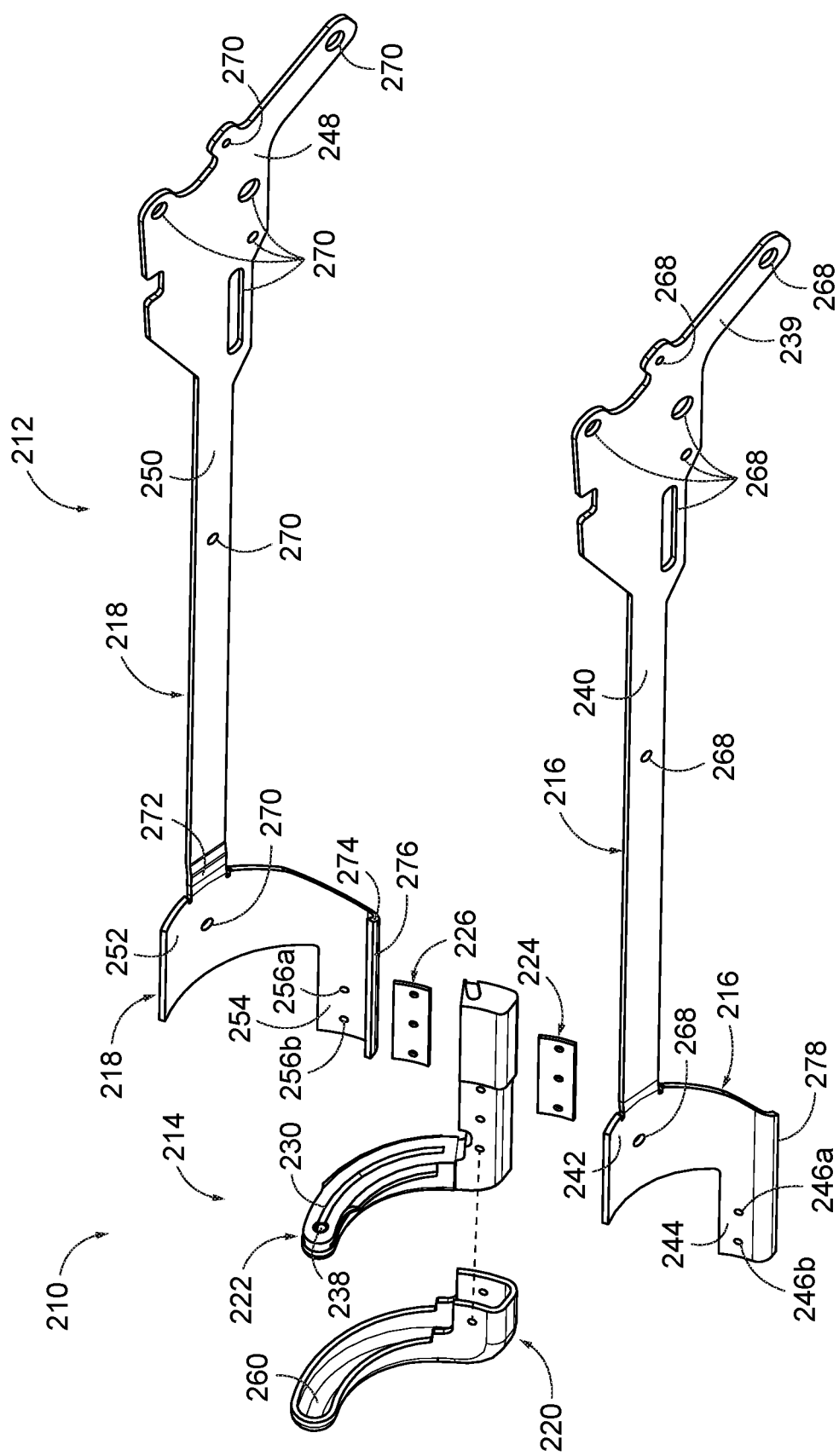
FIG. 5 depicts an exploded right rear perspective view of the frame of FIG. 3, with the frame including left and right handle frames, left and right support plates, a distal anvil support portion, and an insert coupled together with fasteners.
Figure 6:
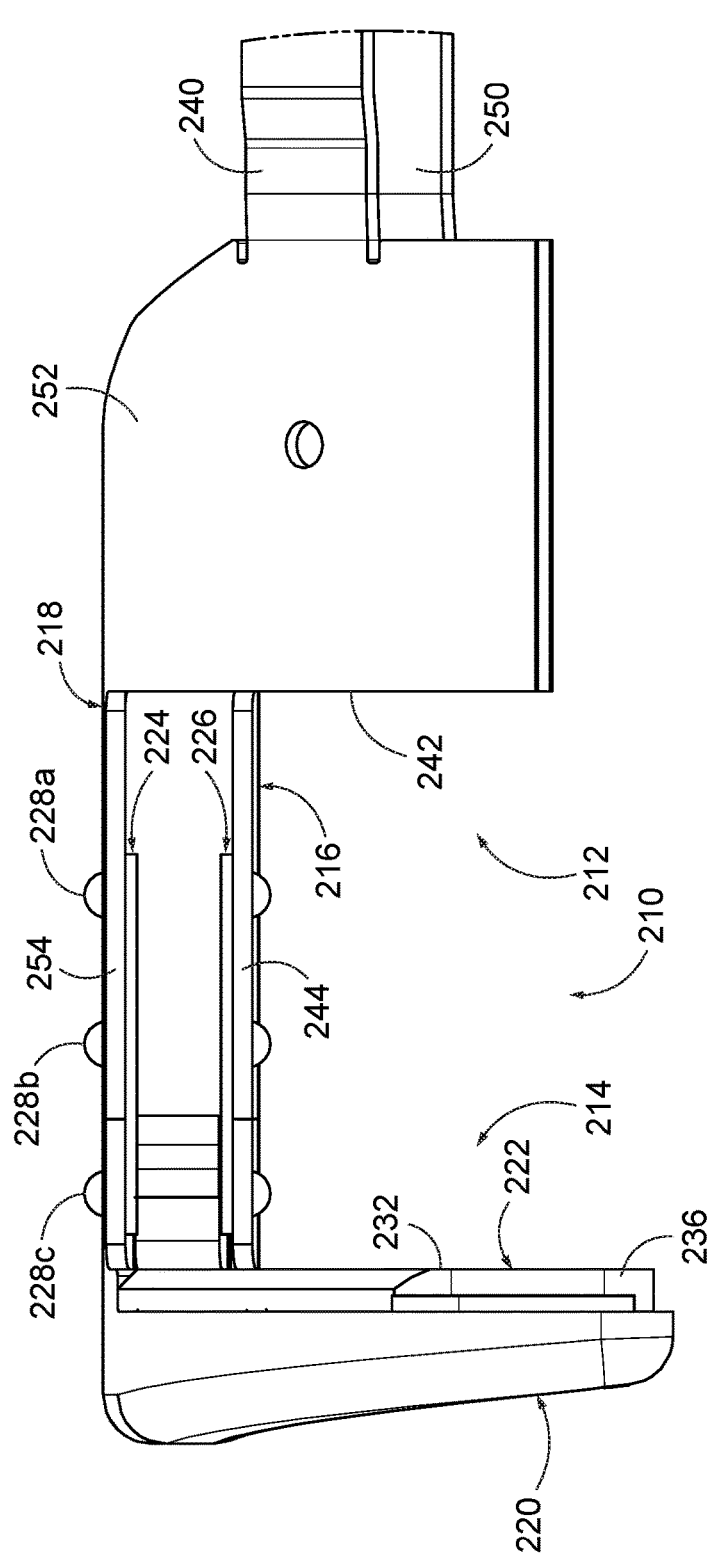
FIG. 6 depicts a left top perspective view of the distal portion of FIG. 4.

FIG. 5 shows an exploded perspective view of frame (210) of FIG. 3, more clearly showing left and right handle frames (216, 218) of shaft frame (212). As shown, left handle frame (216) includes a handle portion (239), an elongate shaft portion (240) extending distally from handle portion (239), a left curvilinear portion (242) extending distally from elongate shaft portion (240), and a connecting portion (244) extending distally from left curvilinear portion (242). Connecting portion (244) includes shaft alignment features (246a-b). Similarly, right handle frame (218) includes a handle portion (248), an elongate shaft portion (250) extending distally from handle portion (248), a right curvilinear portion (252) extending distally from elongate shaft portion (250), and a connecting portion (254) extending distally from right curvilinear portion (252). Connecting portion (254) includes shaft alignment features (256a-b). Connecting portion (254) includes shaft alignment features (256a-b). As shown, shaft alignment features (246a-b, 256a-b) are apertures extending completely through connecting portion (244); however, other shaft alignment features (246a-b, 256a-b) are also envisioned (e.g. projections and corresponding recesses etc.). Left and right handle frames (216, 218) may be manufactured using a variety of methods, including one or more stamping processes, such as those discussed in greater detail with reference to FIG. 32.

As shown in FIG. 5, end effector frame (214) includes distal anvil support portion (220), insert (222), and left and right support plates (224, 226). Distal anvil support portion (220) includes an alignment feature (258) and a curvilinear cavity (260) configured to receive insert (222). As previously described with respect to supporting structure (128), curvilinear cavity (260) is C-shaped. The C-shaped construction facilitates enhanced functionality and access to tissue within the patient. The term "C-shaped" includes a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure. Similarly, insert (222) includes insert alignment features (262a-c). End effector frame (214) includes left and right support plates (224, 226). Left support plate (224) may include alignment features (264a-c), and right support plate (226) may include alignment features (266a-c). While alignment features (262a-c, 264a-c, 266a-c) are shown as apertures extending completely through, other shaft alignment features (246a-b) are also envisioned.

Figure 8:
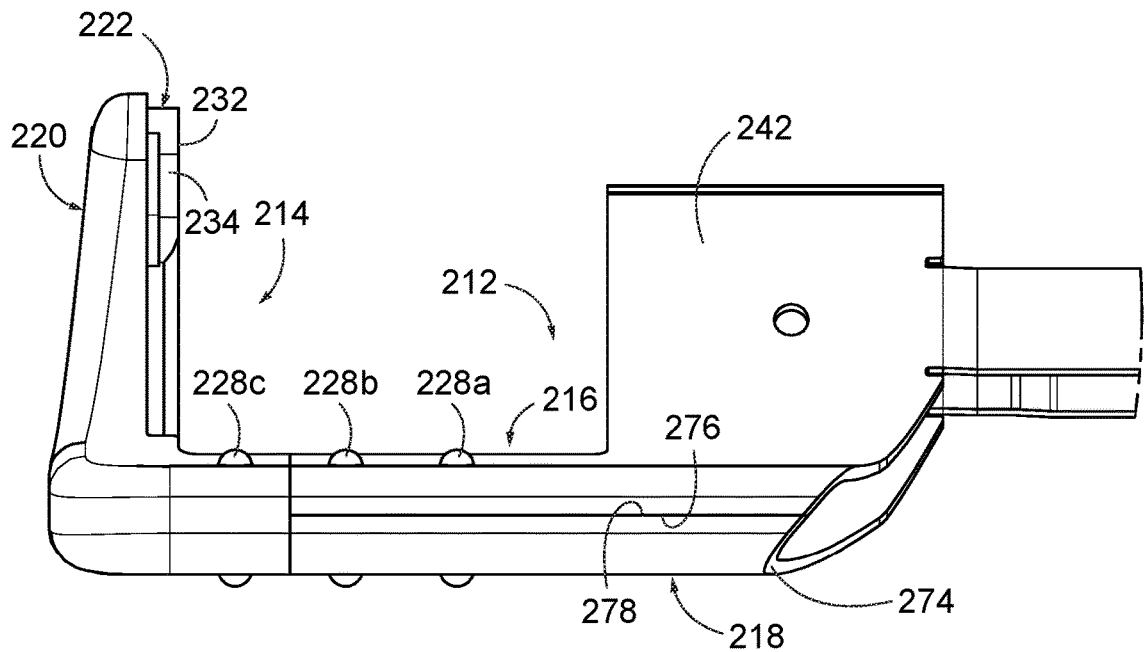
FIG. 8 depicts a right bottom perspective view of the distal portion of FIG. 4.
Figure 9:
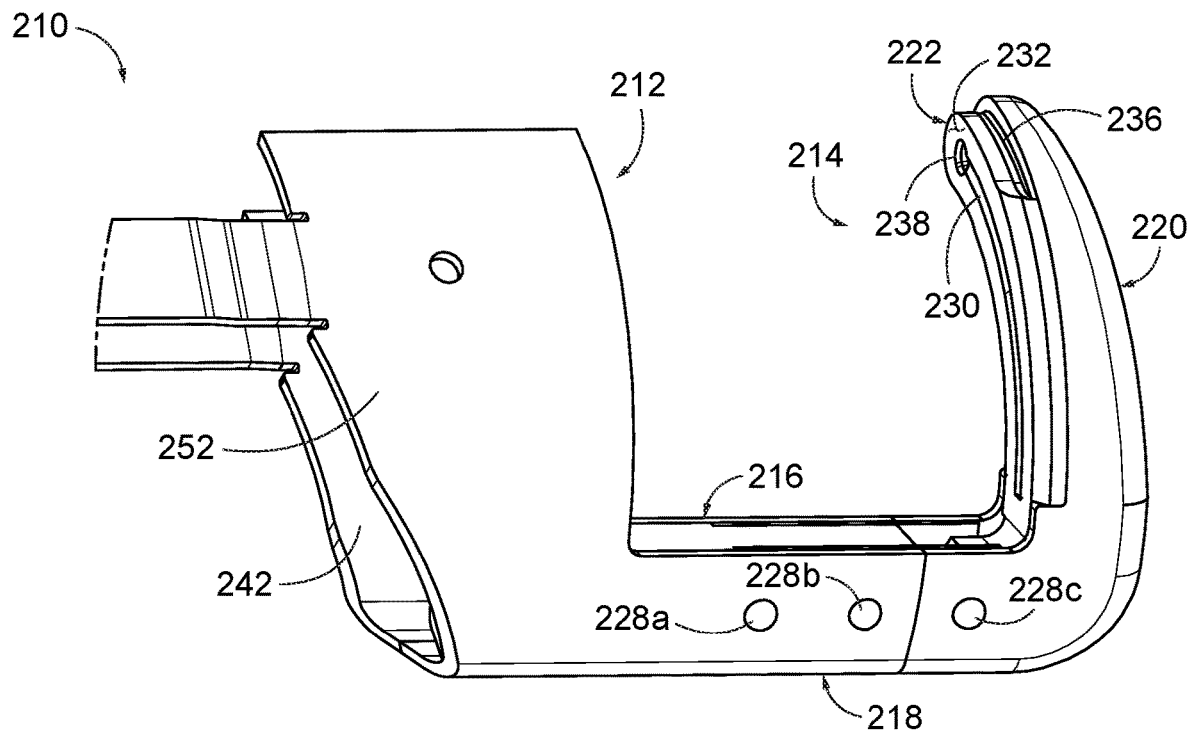
FIG. 9 depicts a left rear perspective view of the distal portion of FIG. 4.

As shown in FIG. 5, left and right handle frames (216, 218) may include a plurality of apertures (268, 270) that perform one or more functions for the operability of instrument (10). Additionally, right handle frame (218) includes an inwardly bending portion (272) as elongate shaft portion (250) transitions to right curvilinear portion (252). As shown in FIGS. 5 and 8, right handle frame (218) includes a curved portion (274) having a longitudinally extending edge (276) that is configured to mate with a longitudinally extending edge (278) of left handle frame (216).

Figure 7:
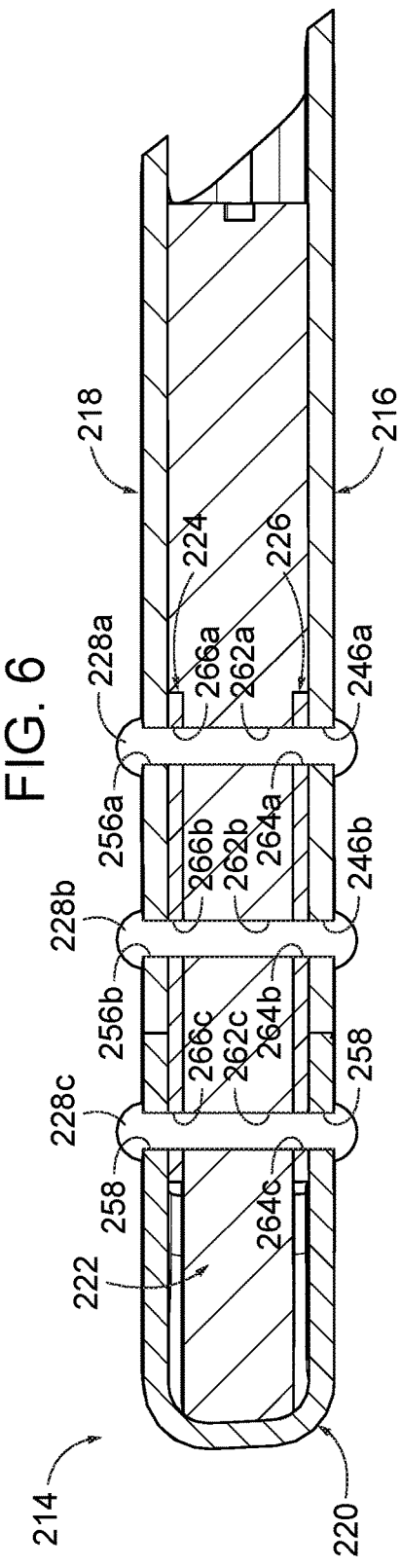
FIG. 7 depicts a left top sectional view of the distal portion of FIG. 6 with fasteners coupling the frame together.

FIGS. 6-9 show various perspective views of the distal portion of frame (210) illustrating fasteners (228a-c). As shown, fasteners (228a-b) are configured to couple left and right handle frames (216, 218), left and right support plates (224, 226), and insert (222) together. As shown in FIG. 7, fastener (228a) couples shaft alignment feature (246a) of left handle frame (216), alignment feature (264a) of left support plate (224), insert alignment feature (262a) of insert (222), alignment feature (266a) of right support plate (226), and shaft alignment feature (256a) of right handle frame (218). Similarly, fastener (228b) couples shaft alignment feature (246b) of left handle frame (216), alignment feature (264a) of left support plate (224), insert alignment feature (262b) of insert (222), alignment feature (266b) of right support plate (226), and shaft alignment feature (256b) of right handle frame (218). Fastener (228c) is configured to couple distal anvil support portion (220), left and right support plates (224, 226), and insert (222) together. More specifically, fastener (228c) couples alignment feature (258) of distal anvil support portion (220), alignment feature (264c) of left support plate (224), insert alignment feature (262c) of insert (222), alignment feature (266c) of right support plate (226), and alignment feature (258) of distal anvil support portion (220). As shown, fasteners (228a-c) are flanged welds; however, fasteners may include, for example, welds, screws, or any other suitable fastener.

B. Second Exemplary Frame

Figure 10C:
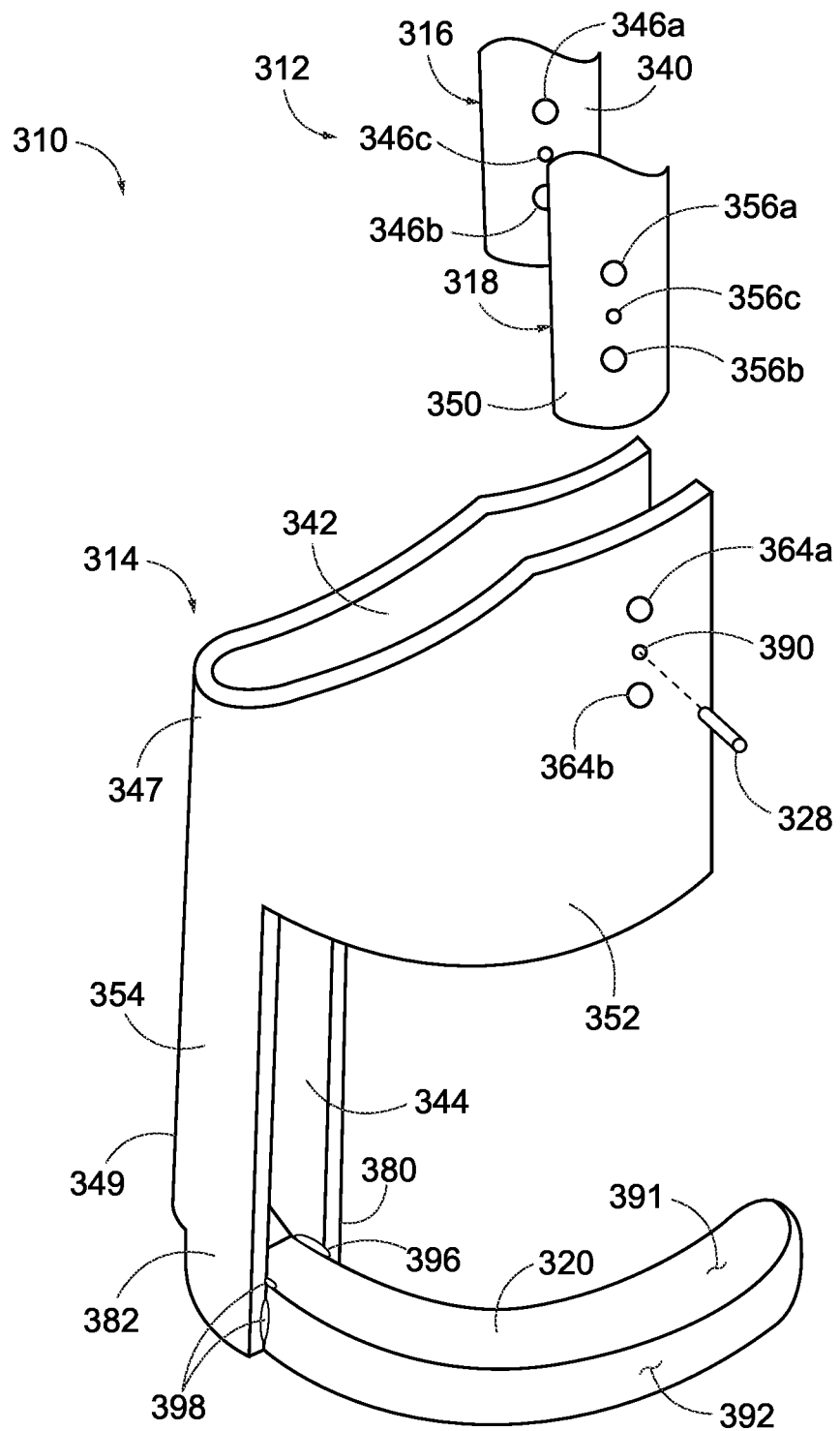
FIG. 10C depicts a perspective view of the distal portion of the frame of FIG. 10B after being bent and welded and coupled with a shaft frame.

FIG. 10A-10C show perspective views of a second exemplary frame (310) that may be incorporated into the surgical stapling instrument (10) of FIG. 1. FIG. 10A-10C show end effector frame (314) at different manufacturing stages. More specifically, FIGS. 10A-10B show end effector frame (314a-b), while FIG. 10C shows an exploded perspective view of frame (310) as including a shaft frame (312) and end effector frame (314). Shaft frame (312) is similar in structure and function to shaft frame (412) described in greater detail below with reference to FIGS. 12-14.

FIG. 10A shows an end effector frame (314a), which will subsequently be formed into end effector frame (314), already being cut from a planar sheet of material, but prior to being bent into the desired shape using one or more bending processes as shown in FIGS. 10B-10C. As shown in FIG. 10A, end effector frame (314) includes left, central, and right curvilinear portions (342, 347, 352), left, central, and right connecting portions (344, 349, 354) extending distally from respective left, central, and right curvilinear portions (342, 347, 354), and a distal anvil support portion (320) extending distally from central connecting portion (349). Left and right connecting portions (344, 354) respectively include left and right alignment features, shown as left and right distally extending flanges (380, 382). Distal anvil support portion (320) includes left and right outwardly extending portions (384, 386) adjacent central connecting portion (349).

At least one of left and right connecting portions (344, 354) (similar to FIG. 3) or left and right curvilinear portions (342, 354) (similar to FIG. 12) may include alignment features configured to align with alignment features (346a-c, 356a-c) of shaft frame (312). As shown in FIG. 10A, left curvilinear portion (342) includes alignment features (362a-b) and an aperture (388). Right curvilinear portion (352) includes alignment features (364a-b) and an aperture (390). However, alignment features (362a-c, 364a-c) and apertures (388, 390) may be omitted, such that shaft frame (312) may be coupled with end effector frame (314) using another method (e.g. welding). Central curvilinear portion (347) and central connecting portion (349) effectively form a spine for end effector frame (314a). As shown, end effector frame (314a) is integrally formed as a unitary piece from a single sheet of material (e.g. metal).

FIG. 10B shows a perspective view of end effector frame (314b) after end effector frame (314a) of FIG. 10A is partially bent. As shown, left and right curvilinear portions (342, 352) exhibit a curvilinear shape that is further bent in FIG. 10C. Stamping includes a variety of forming manufacturing processes, such as punching (using a machine press or stamping press), blanking, embossing, bending, flanging, and coining. As used herein, stamping is intended to refer to the process(es) of placing a workpiece (e.g. a metal sheet, blank) into a stamping press where a tool surface and a die surface converge to form the material into a net shape. While end effector frame (314a) is shown as being planar after blanking, end effector frame (314a) may already be at least partially bent during the blanking process.

Aligning features, shown as aligning lines 389 in FIGS. 10A-10B, may be imparted in end effector frame (314a) prior to bending effector frame (314a). Aligning lines 389 may be applied to the surface using a marking instrument (e.g. marker, pencil, etc.) or carved into the material (e.g. laser etc.). Alternatively, aligning lines 389 may be imparted by one or more of the stamping operations. FIG. 11 shows a sectional view of distal anvil support portion (320) of an end effector frame (314b) of FIG. 10B taken along line 11-11 of FIG. 10B. As shown, distal anvil support portion (320) includes an upper surface (390), a left lateral surface (392), and a right lateral surface (394). As such, distal anvil support portion (320) forms an inverted U-shaped channel.

FIG. 10C shows a perspective view of end effector frame (314) after being further bent and welded. FIG. 10C shows shaft frame (312) as including first and second shaft frame portions, shown as left and right handle frames (316, 318). As previously discussed, left and right handle frames (316, 318) may be similar to left and right handle frames (416, 418) discussed below with reference to FIGS. 12 and 14. End effector frame (214) includes distal anvil support portion (320). An insert, similar to insert (222) that includes C-shaped track (230), may be incorporated into distal anvil support portion (320), similar to how insert (222) was inserted into distal anvil support portion (220). Fastener (328), such as a shoulder rivet similar to shoulder rivet (129), is configured to couple apertures (388, 390) of left and right curvilinear portions (342, 352) with shaft alignment features (346c, 356c) of left and right handle frames (316, 318). Other methods of coupling shaft frame (312) with end effector frame (314) are also envisioned (e.g. welding).

As shown in FIG. 10C, distal anvil support portion (320) is bent proximally, such that upper surface (391) of distal anvil support portion (320) extends generally perpendicular to left and right curvilinear portions (342, 352). Left distally extending flange (380) is welded at a distal end to left outwardly extending portion (384) and/or left lateral surface (392) using a weld (396). Similarly, right distally extending flange (382) is welded at a distal end to right outwardly extending portion (386) and/or right lateral surface (394) using a weld (398). Welds (396, 398) longitudinally and rotatably secure distal anvil support portion (320) with left, central, and right connecting portions (344, 349, 354). Moreover, welding left and right distally extending flanges (380, 382) and/or left and right lateral surfaces (392, 394) to distal anvil support portion (320) improves the mating of these distal features and tightens the tolerance of the radius of curvature of distal anvil support portion (320).

C. Third Exemplary Frame

Figure 14:
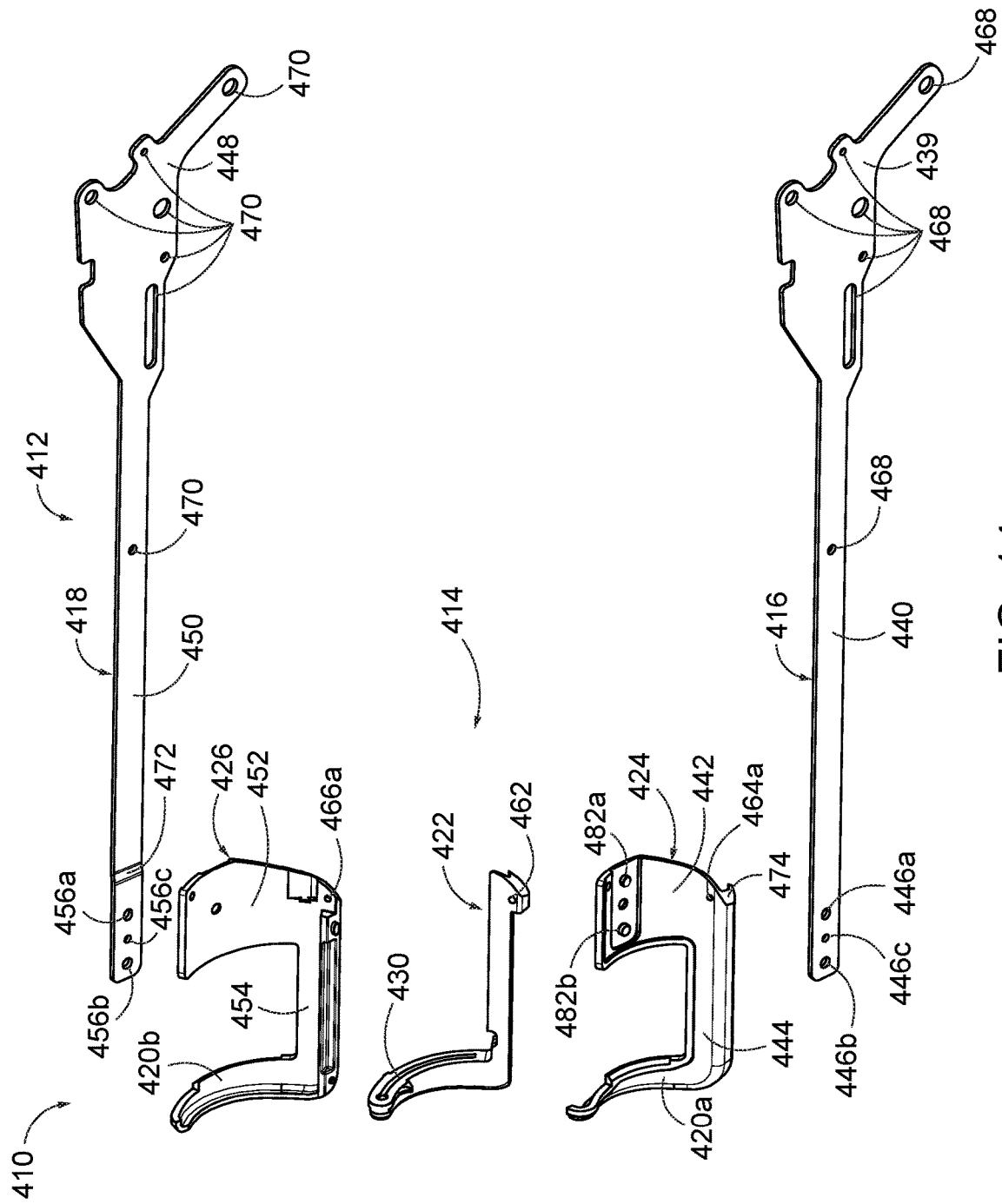
FIG. 14 depicts an exploded right rear perspective view of the frame of FIG. 12, where the frame includes left and right handle frames, left and right end effector frame portions, and an insert.
Figure 20:
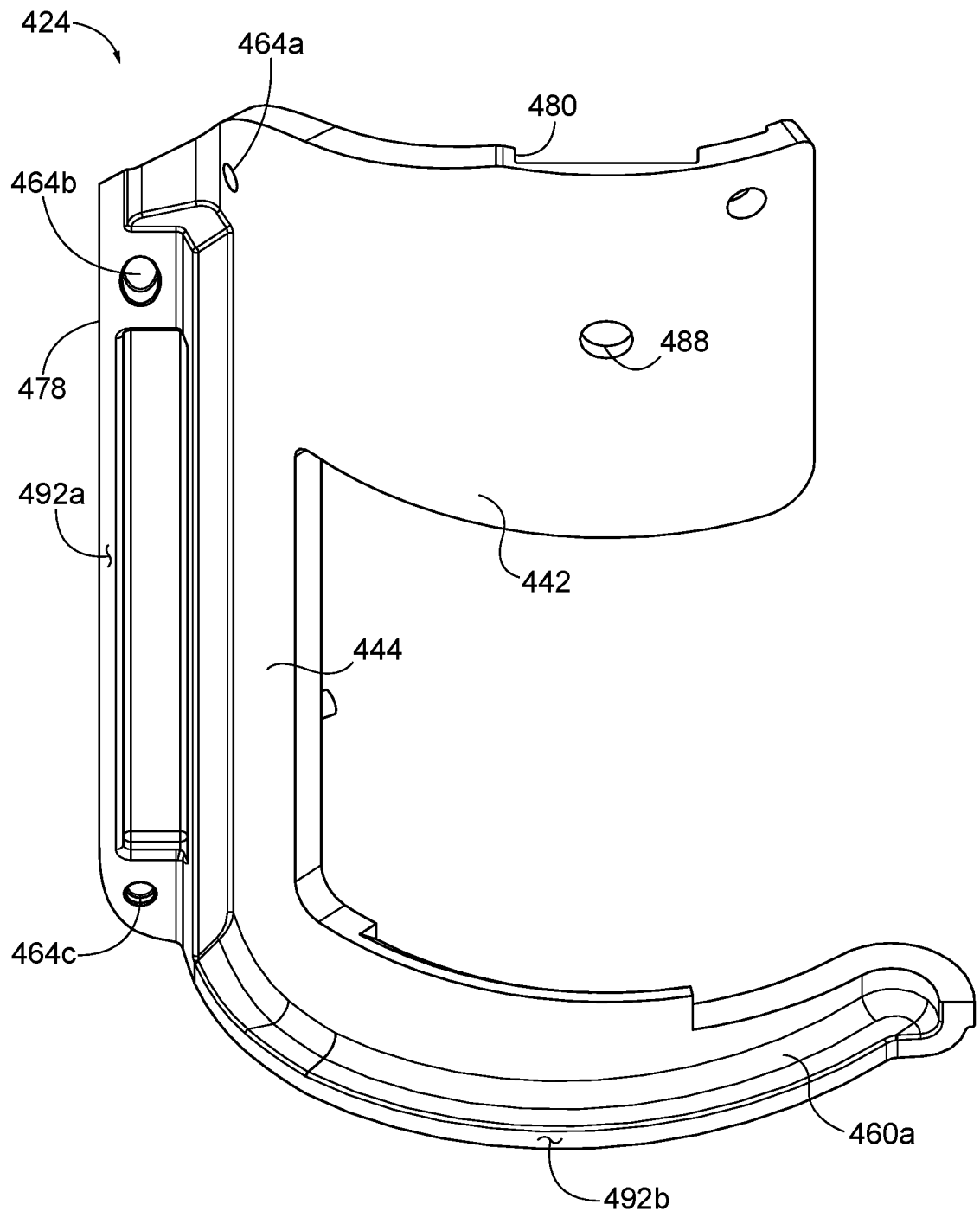
FIG. 20 depicts left perspective view of a left end effector frame portion of FIG. 14.
Figure 23:
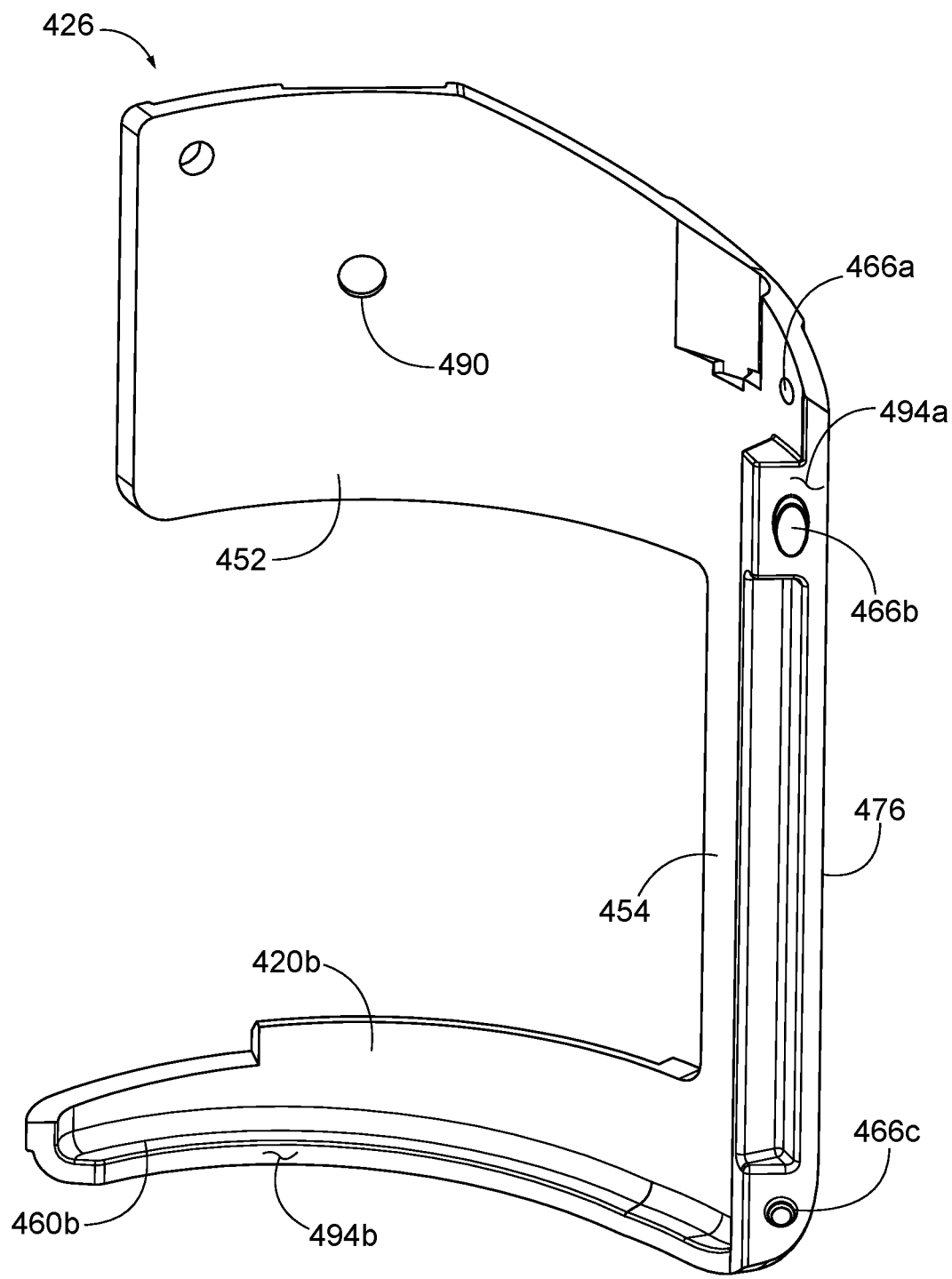
FIG. 23 depicts right perspective view of the right effector frame portion of FIG. 14.
Figure 25:
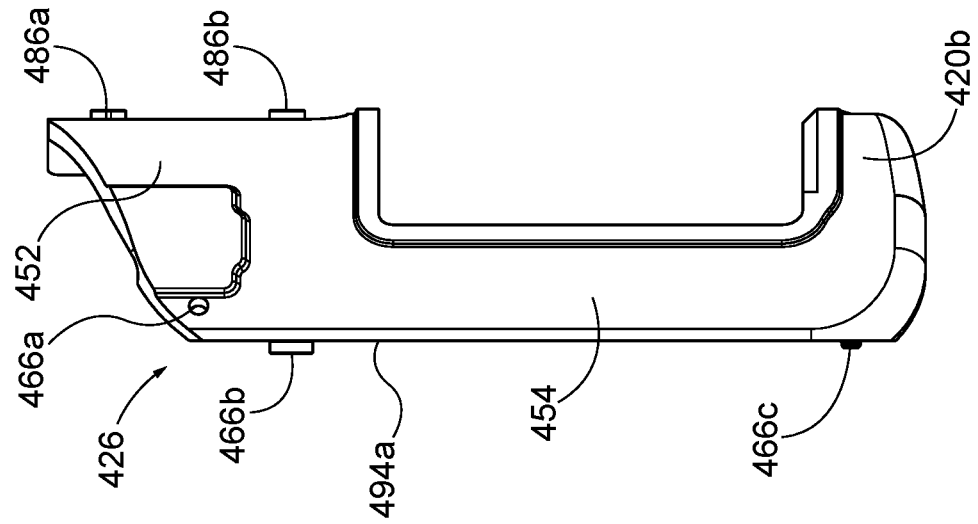
FIG. 25 depicts a rear plan view of the right effector frame portion of FIG. 23.
Figure 24:
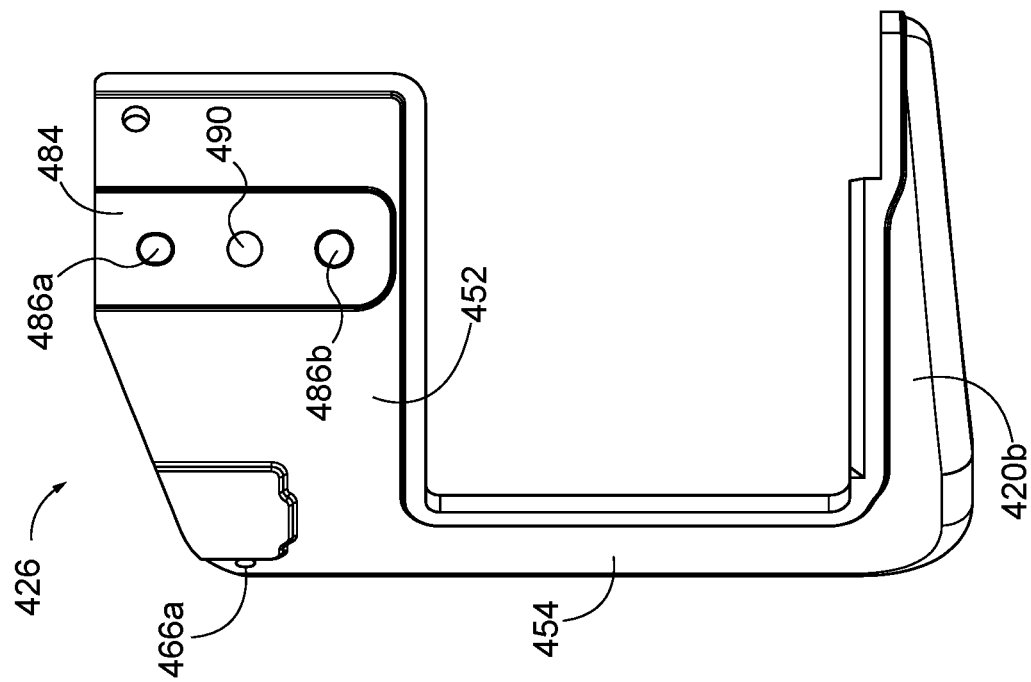
FIG. 24 depicts a left plan view of the right effector frame portion of FIG. 23.
Figure 28:
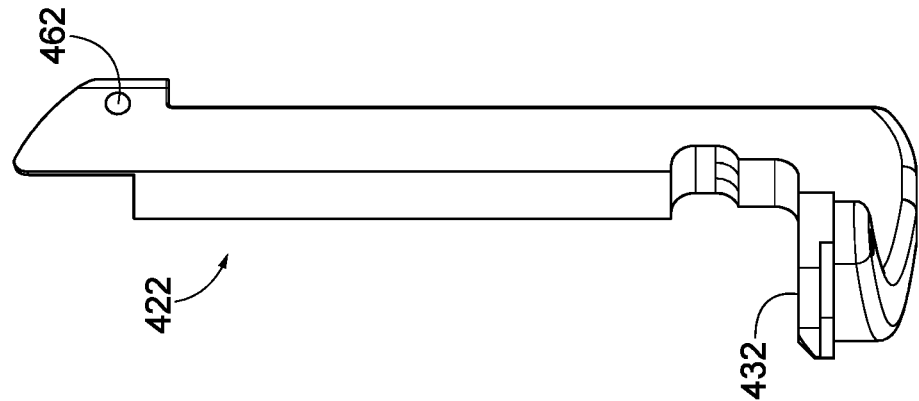
FIG. 28 depicts a right plan view of the insert of FIG. 26.
Figure 27:
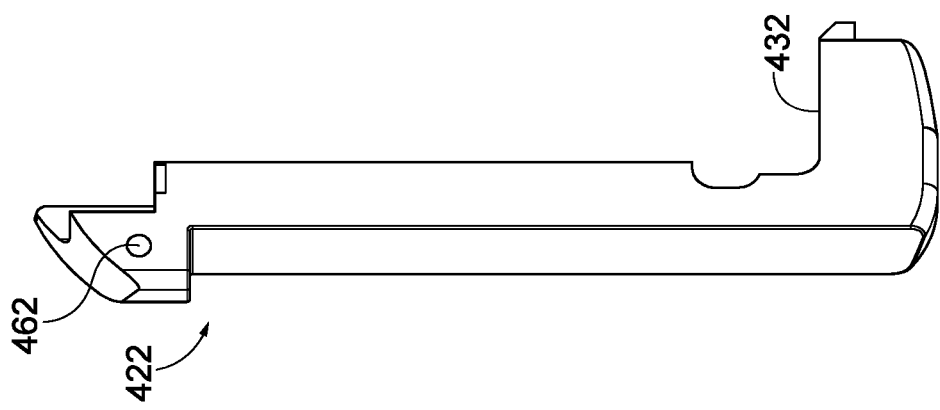
FIG. 27 depicts a rear plan view of the insert of FIG. 26.
Figure 26:
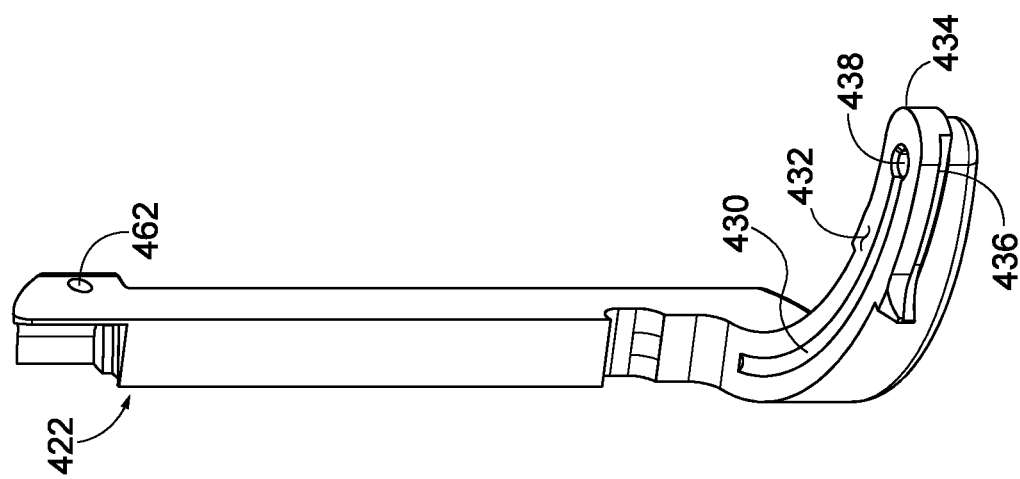
FIG. 26 depicts a left front perspective view of the insert of FIG. 14.

FIGS. 12-28 show a third exemplary frame that may be incorporated into surgical stapling instrument (10) of FIG. 1. FIGS. 12 and 14 show frame (410) as including a shaft frame (412) and an end effector frame (414) that extends distally from shaft frame (412). Shaft frame (412) includes first and second shaft frame portions, shown as left and right handle frames (416, 418). End effector frame (414) includes an insert (422), and left and right end effector portions (424, 426). FIGS. 20-22 show left end effector frame portion (424), FIGS. 23-25 show right end effector frame portion (426), and FIGS. 26-28 show insert (422) in additional detail for greater clarity.

As shown, left and right handle frames (416, 418), insert (422), and left and right end effector frame portions (424, 426) are each integrally formed as a unitary piece and subsequently coupled together. For example, left and right handle frames (416, 418), insert (422), and left and right end effector frame portions (424, 426) may be separately formed using a variety of processes including metal injection molding. Metal injection molding (MIM) refers to any metalworking process where finely-powdered metal is mixed with a binder material to create a feedstock that is subsequently shaped and solidified using molding process (such as injection molding). Metal injection molding allows for high volume, complex parts to be shaped. As will be described in greater detail below, left and right handle frames (416, 418), insert (422), and left and right end effector frame portions (424, 426) and each of their respective features have a molded shape. Certain features of which may be subsequently machined to a machined shape. Machining certain features may provide many benefits, including improving the dimensional tolerances of the metal injection molding process. However, it is envisioned that if desired, two or more of these components may be integrally formed together as a unitary piece.

FIG. 13 shows an enlarged perspective view of a distal portion of frame (410) of FIG. 12. As shown in FIG. 13 and in greater detail with reference to FIGS. 26-28, insert (422) includes a C-shaped track (430) disposed within an upper surface (432) of insert (422), with left and right flanges (434, 436) separated by upper surface (432). C-shaped track (430) includes an enlarged portion (438) configured to receive a distal portion of retaining pin (40) shown in FIGS. 1A-1D. Insert (422) is configured to receive staple cartridge (28) shown in FIGS. 1A-1D. More specifically, left and right flanges (434, 436) of insert (422) are configured to slidably receive corresponding portions of staple cartridge (28). Similar to insert (222), insert (422) includes an insert alignment feature (462) configured to secure insert (222) with left and right end effector frame portions (424, 426) as discussed in greater detail with reference to FIGS. 15-17. It is envisioned that insert (422) may be formed for a metallic or polymeric material.

FIG. 14 shows an exploded perspective view of frame (410) of FIG. 12, illustrating left and right handle frames (416, 418) of shaft frame (412). As shown, left handle frame (416) includes a handle portion (439) and an elongate shaft portion (440) extending distally from handle portion (439). Elongate shaft portion (440) includes shaft alignment features (446a-c), instead of connecting portion (244) including shaft alignment features (246a-b) as shown in FIG. 5. Similarly, right handle frame (418) includes a handle portion (448) and an elongate shaft portion (450) extending distally from handle portion (448). Elongate shaft portion (450) includes shaft alignment features (456a-c), instead of connecting portion (254) including shaft alignment features (256a-b) as also shown in FIG. 5. While shaft alignment features (446a-c, 456a-c) are shown as apertures, other shaft alignment features (446a-b) are also envisioned (e.g. projections and corresponding recesses etc.). Left and right handle frames (416, 418) may include a plurality of apertures (468, 470) that perform one or more functions for the operability of instrument (10), similar to apertures (268, 270) shown in FIG. 5 with respect to frame (210). Additionally, right handle frame (418) includes an inwardly bending portion (472) as elongate shaft portion (450) transitions to right curvilinear portion (452). It is envisioned that left and right handle frames (416, 418) may be manufactured using a variety of methods, including one or more stamping processes.

FIGS. 14 and 20-22 show additional details of left end effector frame portion (424). Left end effector frame portion (424) includes a left curvilinear portion (442) configured to be coupled with elongate shaft portion (440), a connecting portion (444) extending distally from left curvilinear portion (442), and a left distal anvil support portion (420a) extending distally from left curvilinear portion (442). Left curvilinear portion (442) includes a recessed alignment portion (480) adjacent a proximal end, with alignment posts (482a-b) extending outwardly from recessed alignment portion (480). As shown in FIG. 13, alignment posts (482a-b) are configured to extend through shaft alignment features (446a-b) of elongate shaft portions (440, 450). As shown in FIGS. 20 and 22, left distal anvil support portion (420a) includes a left curvilinear cavity portion (460a) configured to receive a portion of insert (422). Left end effector frame portion (424) includes a curved portion (474) having a longitudinally extending edge (478) that is configured to mate with a longitudinally extending edge (476) of right end effector frame portion (426).

FIGS. 14 and 23-25 show additional details of right end effector frame portion (426). Right end effector frame portion (426) includes a right curvilinear portion (452) configured to be coupled with elongate shaft portion (450), a connecting portion (454) extending distally from right curvilinear portion (452), and a right distal anvil support portion (420b) extending distally from right curvilinear portion (452). Right curvilinear portion (452) includes a recessed alignment portion (484) with alignment posts (486a-b) extending outwardly from recessed alignment portion (480). Alignment posts (486a-b) are configured to extend through shaft alignment features (456a-b). As shown in FIG. 23, right distal anvil support portion (420b) includes a right curvilinear cavity portion (460b) configured to receive another portion of insert (422). As such, left and right curvilinear cavity portions (460a-b) collectively receive a bottom surface of insert (222).

FIGS. 13 and 14 show the coupling of shaft frame (412) with end effector frame (414) in greater detail. As shown, shaft frame (412) and end effector frame (414) are coupled together using a fastener (428), shown as a shoulder rivet similar to rivet (129) in FIGS. 1A-1D. Left and right curvilinear portions (442, 452) include respective apertures (488, 490). Fastener (428) is configured to couple apertures (488, 490) of left and right curvilinear portions (442, 452) with shaft alignment features (446c, 456c) of left and right handle frames (416, 418).

Figure 15:
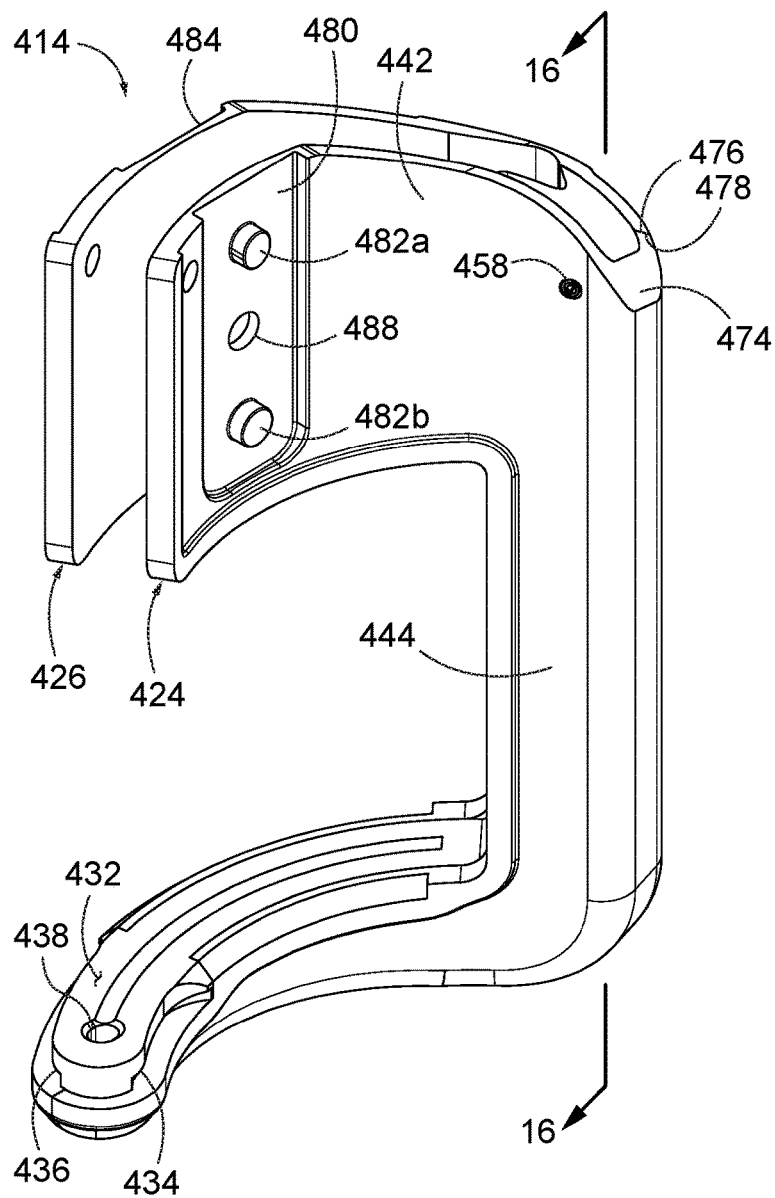
FIG. 15 depicts a top right perspective view of an end effector frame that includes the left and right distal end effector portions and the insert of FIG. 13.
Figure 16:
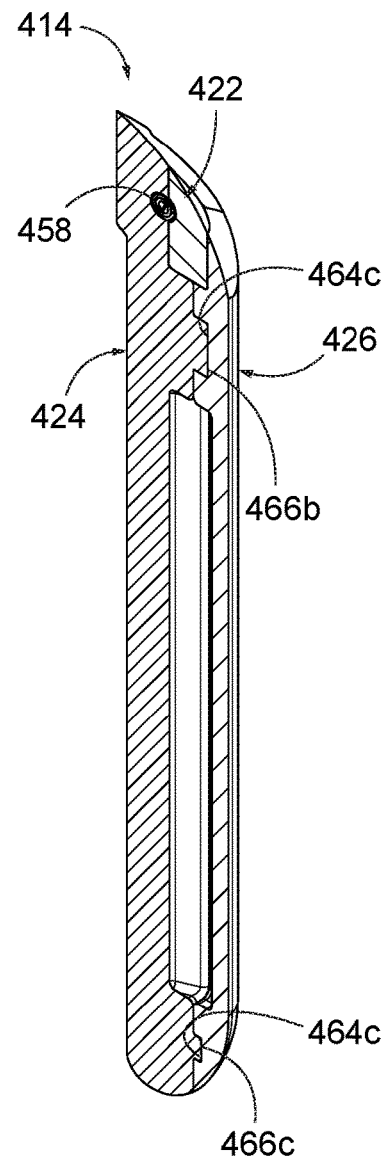
FIG. 16 depicts a top right sectional view of the end effector portion of FIG. 15 including interior alignment features and a fastener.

FIGS. 15-17 show the coupling of left and right end effector frame portion (424, 426) and insert (422). As shown, left end effector frame portion (424) includes alignment features (464a-c) and contacting surfaces (492a-b) configured to contact right end effector frame portion (426). Similarly, right end effector frame portion (426) includes alignment features (466a-c) and contacting surfaces (494a-b) configured to contact left end effector frame portion (424). A fastener, shown as a spring pin (458), is configured to couple insert (422), and left and right end effector frame portions (424, 426) together. As shown in FIG. 16, spring pin (458) extends completely through alignment features (462, 464a, 466a). While alignment features (462, 464a, 466a) are shown as apertures extending completely through the respective insert (222), left end effector frame portion (424), and right end effector frame portion (426), other alignment features are also envisioned.

As shown in FIG. 16 alignment features (462b-c, 464b-c) of left and right end effector frame portions (424, 426) are located between left and right end effector frame portion (424, 426) and not visible along an outer surface of end effector frame (414) once left and right end effector frame portions (424, 426) are coupled together. While alignment features (464b-c) are shown as recesses and alignment features (466b-c) are shown as projections, a variety of other alignment features having various shapes are also envisioned. It is also envisioned that alignment features (464b-c) may be projections and alignment features (466b-c) may be projections. It is also envisioned that alignment features (464b-c) include at least one projection and at least one recess, such that alignment features (466b-c) include at least one corresponding recess and at least one projection.

D. Fourth Exemplary Frame

Figure 29:
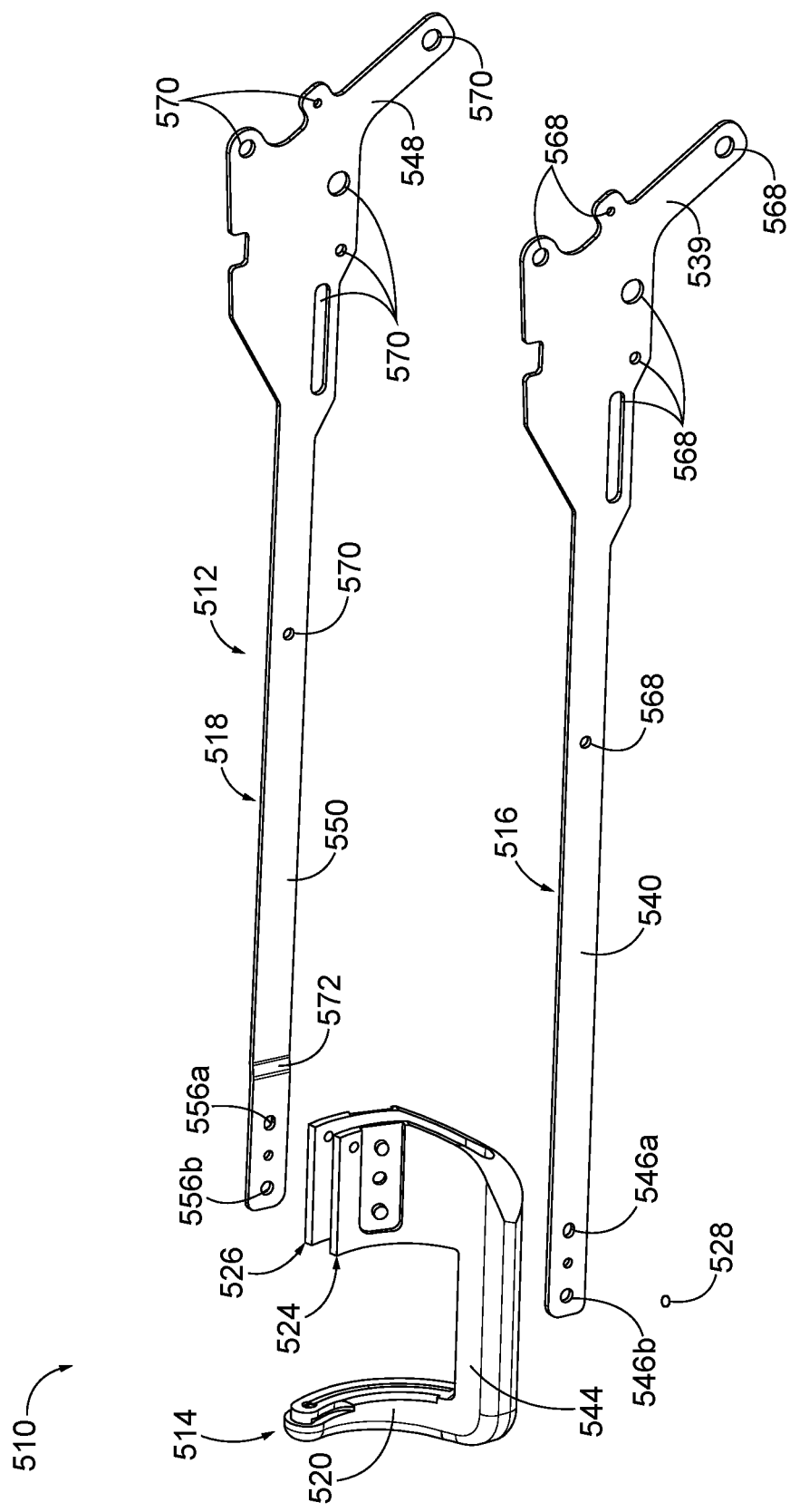
FIG. 29 depicts a right rear perspective view of a fourth exemplary frame that may be incorporated into the surgical stapling instrument of FIG. 1.
Figure 30:
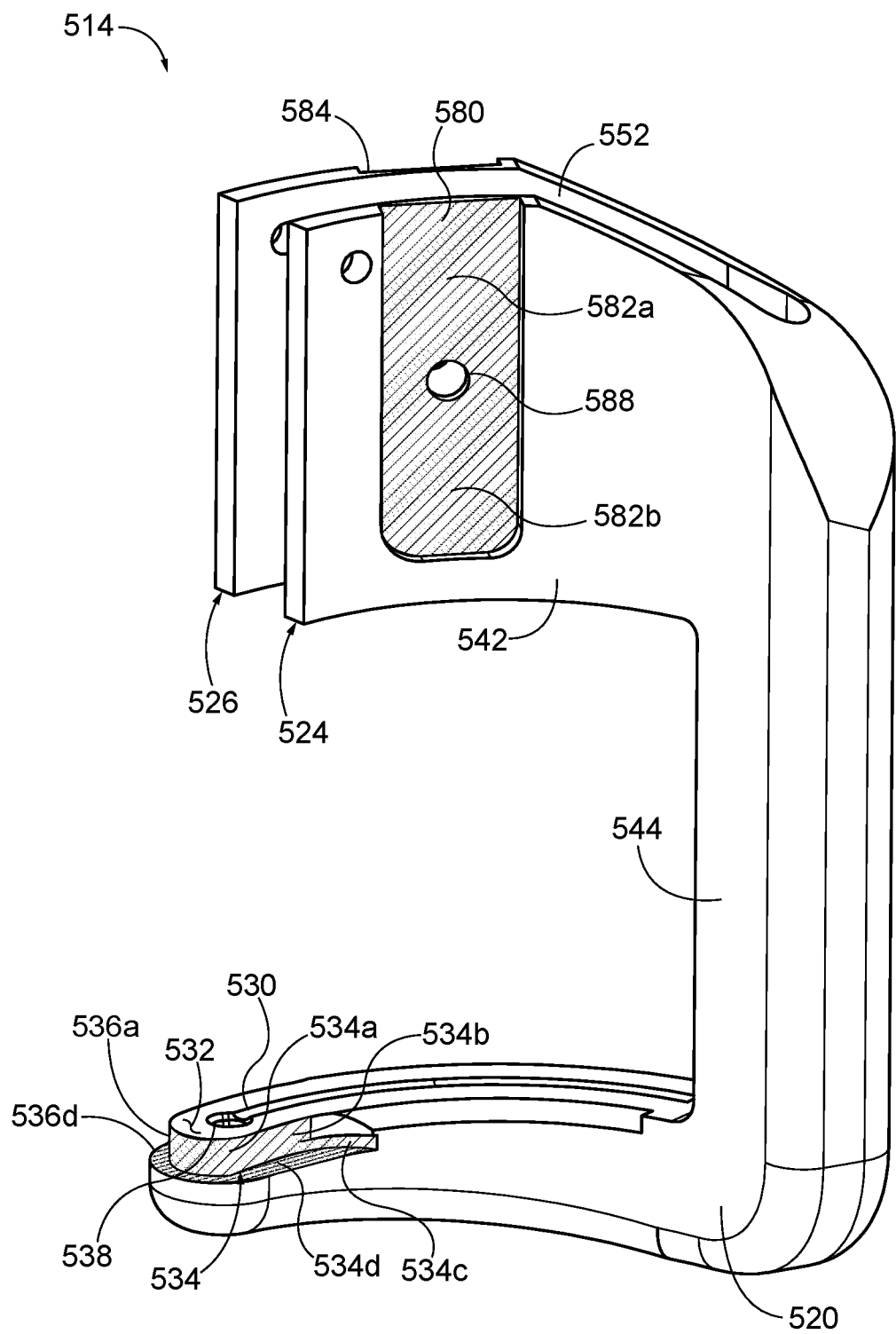
FIG. 30 depicts a right rear perspective view of an end effector frame of the frame of FIG. 29.
Figure 31:
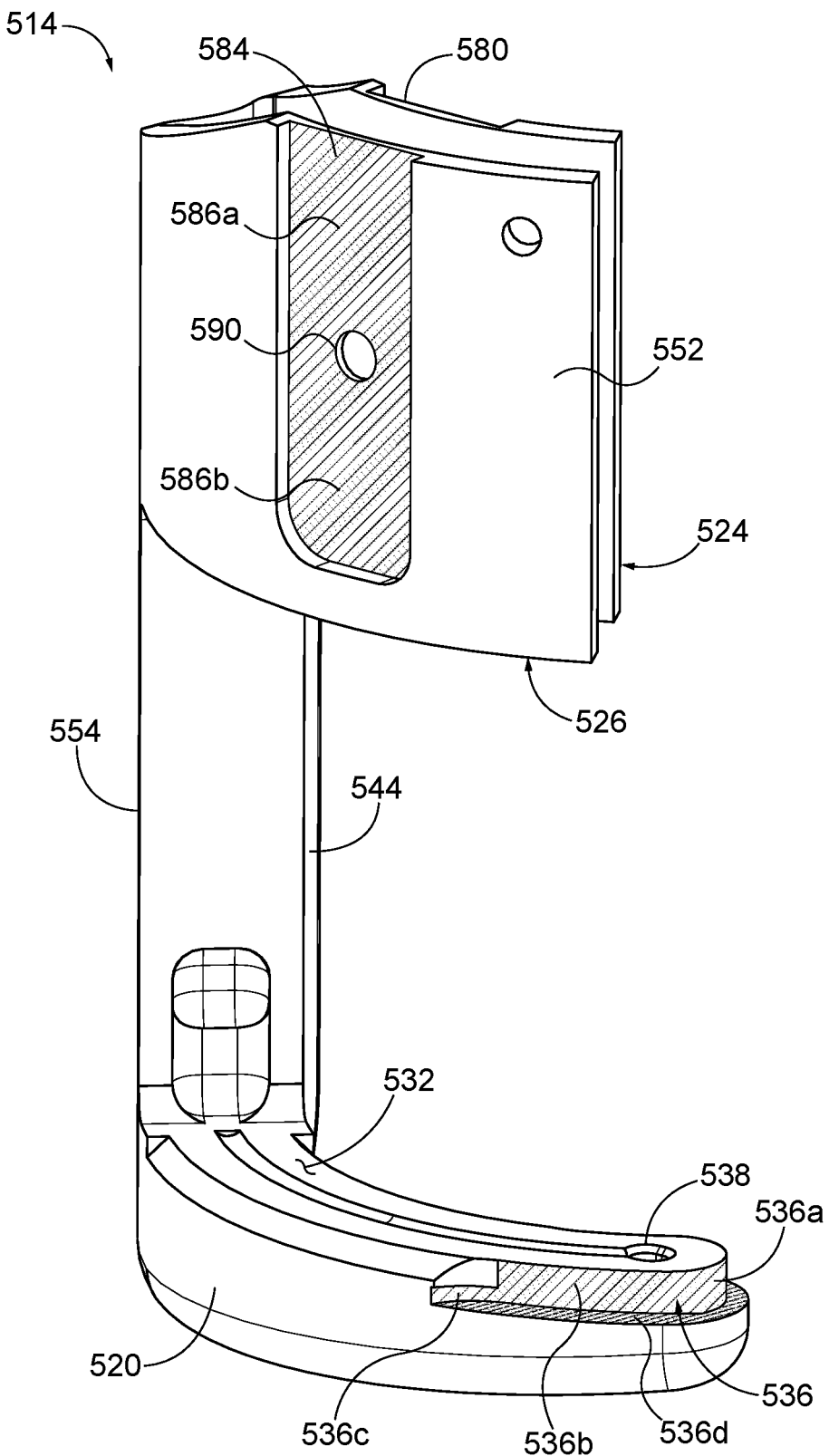
FIG. 31 depicts left rear perspective view of the end effector frame of FIG. 30.

FIGS. 29-31 show a fourth exemplary frame (510) that may be incorporated into the surgical stapling instrument of FIG. 1. FIG. 29 shows frame (510) as including a shaft frame (512) and an end effector frame (514) that extends distally from shaft frame (512) and is coupled with shaft frame (512) using one or more fasteners (528). Shaft frame (512) includes first and second shaft frame portions, shown as left and right handle frames (516, 518). Left handle frame (516) includes handle portion (539), an elongate shaft portion (540), shaft alignment features (546a-b), and apertures (568). Similarly, right handle frame (518) includes a handle portion (548), an elongate shaft portion (550), shaft alignment features (456a-b), and apertures (568).

End effector frame (514) includes a distal anvil support portion (520), a left end effector frame portion (524), right end effector frame portion (526), C-shaped track (530), upper surface (532), left flange (534), right flange (536), enlarged portion (538), left and right curvilinear portions (542, 552), connecting portions (544, 554), recessed portions (580, 584), alignment posts (582a-b, 586a-b), apertures (588, 590). End effector frame (514) may be formed using additive manufacturing, such that end effector frame (514) may be integrally formed together as a unitary piece. Additive manufacturing includes material extrusion, directed energy deposition, material jetting (e.g. 3-D printing), binder jetting, sheet lamination, vat polymerization, and powder bed fusion. Powder bed fusion includes direct metal laser sintering (DMLS), selective laser sintering (SLS), selective heat sintering (SHS), electron beam melting (EBM) and direct metal laser melting (DMLM). As shown, end effector frame (514) is formed using 3-D printing.

Machining specific features may allow for initial molded geometries having better mold flow characteristics for the metal injection molding process. These features may include for example left and right flanges (534, 536), recessed portions (580, 584), alignment posts (582, 586) which are shaded (using hatching) in FIGS. 30-31. As shown, left flange includes leading portion (534a), adjacent a left lateral surface (534b), an arcuate recessed portion (534c), and a lower surface (534d). Similarly, right flange (536) includes leading surface (536a), adjacent a right lateral surface (536b), an arcuate recessed surface (536c), and a lower surface (536d). While each surface (334a-d, 536a-d) is shown as being machined; one or more surfaces (334a-d, 536a-d) may be machined. These machining operations may leave indication marks on the connected side walls that show where machining was used, and the amount of material removed. As such, using a metal injection molding process and subsequent machining provides frame (210, 310, 410, 510) with higher performance machined features on the same distal component. Additionally, method (510) provides a superior surface finish than metal injection molding is capable of alone.

E. First Exemplary Method of Manufacture

Figure 32:
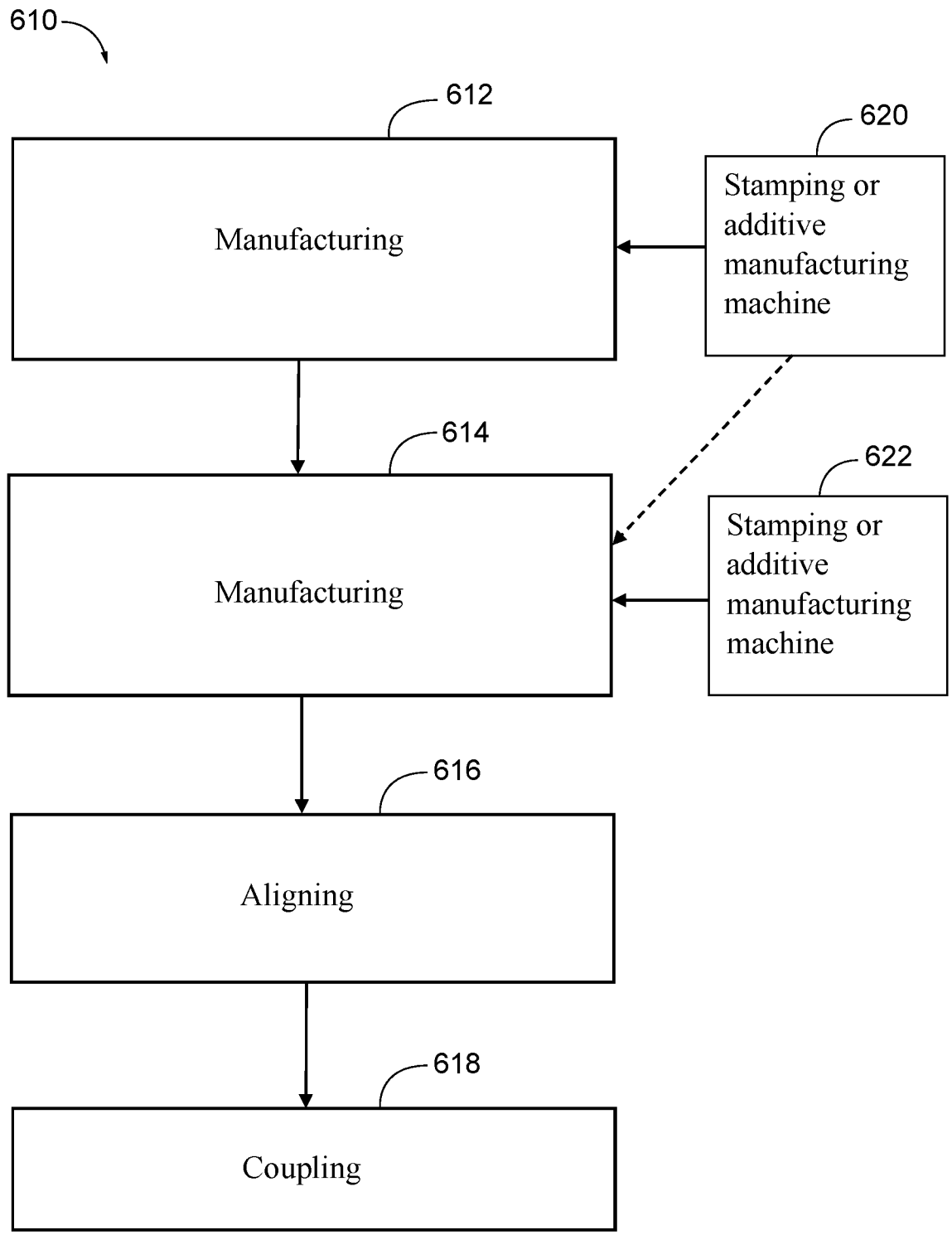
FIG. 32 depicts an exemplary method of manufacturing the frame of FIG. 3 that may be incorporated into the surgical stapling instrument of FIG. 1.

FIG. 32 shows a first exemplary method (610) of manufacturing frame (210, 310, 410, 510) of surgical instrument (10) that includes steps (612, 614, 616, 618, 620). As shown, at step (612), method (610) includes manufacturing a first portion of frame (210, 310, 410, 510) of surgical instrument

(10) using a stamping or additive manufacturing machine (622). First portion includes a first curvilinear portion ((e.g. curvilinear portions (242, 252, 242, 352, 442, 452, 542, 552)) of an end effector frame (214, 314, 414, 514) and a first alignment feature. For example, manufacturing the first portion may include stamping or using additive manufacturing (e.g. metal injection molding, 3-D printing) of the first portion.

As shown, at step (614), method (610) includes manufacturing a second portion of frame (210, 310, 410, 510) of surgical instrument (10) using a stamping or additive manufacturing machine (624). Second portion includes a second alignment feature. For example, manufacturing the second portion may include stamping, metal injection molding, or 3-D printing the second portion. As shown, at step (616), method (610) includes manufacturing a third portion of frame (210, 310, 410, 510) of surgical instrument (10) separate from either of the first or second portions. The third portion includes a C-shaped track (230, 430, 530). Third portion may be manufactured, for example, from metal using metal injection molding or from a polymeric material using an injection molding machine (626). As shown, at step (618), method (610) includes aligning the first portion with the second portion by aligning first and second alignment features of first and second portions of instrument (10) together. As shown, at step (620), method (610) includes coupling first and second portions of frame (210, 310, 410, 510) of instrument (10) together.

F. Second Exemplary Method of Manufacture

Figure 33:
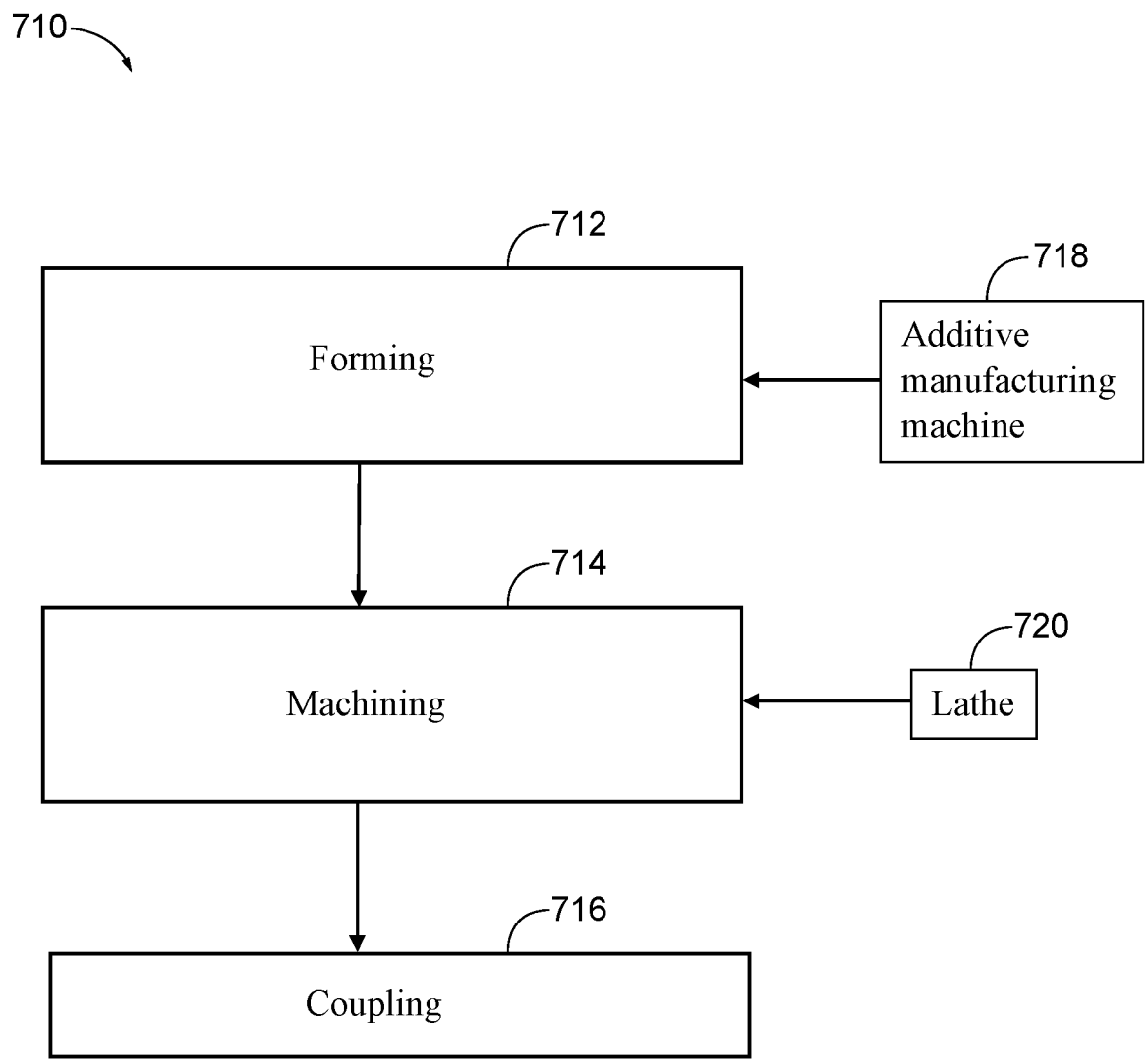
FIG. 33 depicts an exemplary method of manufacturing the frame of FIG. 14 that may be incorporated into the surgical stapling instrument of FIG. 1.

FIG. 33 shows a second exemplary method (710) of manufacturing frame (410, 510) of surgical instrument (10) that includes steps (712, 714, 716). As shown, at step (712), method (710) includes forming end effector frame (414, 514) of frame (410, 510) using additive manufacturing. As shown, an additive manufacturing machine (718) (e.g. a metal injection molding machine or 3-D printer) may be used. End effector frame (414, 514) has at least one feature having an initial shape. As previously indicated, additive manufacturing includes material extrusion, directed energy deposition, material jetting (e.g. 3-D printing), binder jetting, sheet lamination, vat polymerization, and powder bed fusion. Powder bed fusion includes direct metal laser sintering (DMLS), selective laser sintering (SLS), selective heat sintering (SHS), electron beam melting (EBM) and direct metal laser melting (DMLM). As shown, end effector frame (514) is formed using 3-D printing.

As shown, at step (712), method (710) includes machining at least one feature of end effector frame (414, 514) to have a machined shape without machining entire end effector frame (414, 514) using a lathe (720). Machining removes material from at least one feature (e.g. left and right flanges (434, 436, 534, 536), recessed portion (480, 484, 580, 584), alignment posts (482, 486, 582, 586)), such that the dimensions of the initial shape are greater than the dimensions of the machined shape of the at least one feature. Other features may also be machined where enhanced properties are desired. As shown, at step (714), method (710) includes coupling end effector frame (414, 514) into surgical instrument (10).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing a frame of a curved surgical stapler comprising: (a) manufacturing a first portion of the frame of the curved surgical stapler, wherein the first portion includes a first curvilinear portion of an end effector and a first alignment feature; (b) manufacturing a second portion of the frame of the curved surgical stapler separate from the first portion, wherein the second portion includes a second alignment feature; (c) manufacturing a third portion of the frame of the curved surgical stapler separate from either of the first or second portions, wherein the third portion includes a C-shaped track; (d) aligning the first portion with the second portion by aligning the first and second alignment features of the first and second portions of the curved surgical stapler; and (e) coupling the first and second portions of the frame of the curved surgical stapler together.

Example 2

The method of Example 1, wherein manufacturing the first and second portions further comprises metal injection molding, 3-D printing or stamping the first and second portions.

Example 3

The method of Example 2, wherein stamping the first portion further comprises cutting the first portion from a planar sheet of the material and subsequently bending the first portion.

Example 4

The method of Example 3, further comprising: imparting aligning lines in the first portion prior to bending the first portion along the aligning lines.

Example 5

The method of any one or more of Examples 3 through 4, wherein the first portion includes a second curvilinear portion of the end effector, a connecting portion extending distally from the first and second curvilinear portions of the end effector, and a distal anvil support portion extending distally from the connecting portion, wherein stamping the first portion further comprises bending the first and second curvilinear portions of the end effector, the connecting portion, and the distal anvil support portion.

Example 6

The method of Example 5, further comprising: welding first and second distal ends of the connecting portion to the distal anvil support portion using at least one weld.

Example 7

The method of any one or more of Examples 1 through 4, further comprising: manufacturing a third portion of the frame, wherein the third portion includes a third alignment feature configured to align with the first and second alignment features of the first and second portions.

Example 8

The method of Example 7, wherein aligning the first portion with the second portion further comprises aligning the first, second, and third portions together using the first, second, and third alignment features.

Example 9

The method of Example 8, wherein coupling the first and second portions together further comprises inserting a fastener into the first, second, and third alignment features of the first, second, and third portions.

Example 10

The method of any one or more of Examples 1 through 4 and Examples 6 through 9, wherein the first portion includes a first connecting portion extending distally from the first curvilinear portion, and a first distal anvil support portion extending distally from the first connecting portion, wherein the second portion includes a second curvilinear portion, a second connecting portion extending distally from the second curvilinear portion, and a second distal anvil support portion extending distally from the second connecting portion.

Example 11

The method of any one or more of Examples 1 through 10, wherein the first and second portions of the frame are completely separate from each other prior to coupling first and second portions together.

Example 12

The method of any one or more of Examples 1 through 4 and Examples 6 through 11, wherein the second portion includes a second curvilinear portion, wherein the first and second alignment features of the first and second portions are located between the first and second portions and not visible along an outer surface of the frame once the first and second portions are coupled together.

Example 13

The method of any one or more of Examples 1 through 12, wherein the first alignment feature of the first portion includes at least one projection or at least one recess, wherein the second alignment feature of the second portion includes the other of the projection or the recess.

Example 14

The method of any one or more of Examples 1 through 13, further comprising: stamping a first handle frame including a first shaft alignment feature; stamping a second handle frame including a second shaft alignment feature; coupling the first portion to the first handle frame by coupling the first alignment feature of the first portion with the first shaft alignment feature using at least one fastener; and coupling the second portion to the second handle frame by coupling the second alignment feature of the second portion with the second shaft alignment feature using at least one fastener.

Example 15

The method of Example 14, wherein the first handle frame comprises a first elongate shaft portion and a first handle portion, wherein the second handle frame comprises a second elongate shaft portion and a second handle portion.

Example 16

A method of manufacturing an end effector frame of a curved surgical stapler, the method comprising: (a) forming the end effector frame using additive manufacturing, wherein the end effector frame has at least one feature having an initial shape; (b) machining the at least one feature of the end effector frame to have a machined shape without machining the entire end effector frame; and (c) coupling the end effector frame into the curved surgical stapler.

Example 17

The method of Example 16, wherein the machining removes material from the at least one feature, such that the dimensions of the initial shape are greater than the dimensions of the machined shape of the at least one feature.

Example 18

The method of any one or more of Examples 16 through 17, further comprising: machining first and second recessed portions, wherein each of the first and second recessed portions each include at least one coupling feature; and coupling the alignment features of the first and second recessed portions to the end effector frame to the curved surgical stapler.

Example 19

A frame of a curved surgical stapler comprising: (a) an end effector frame; (b) a shaft frame extending proximally from the end effector frame, wherein the shaft frame includes: (i) a first portion that includes a first curvilinear portion and a first alignment feature, (ii) a second portion that includes a second curvilinear portion a second alignment feature, and (c) a fastener configured to couple the first and second alignment features of the first and second portions together.

Example 20

The frame of Example 19, wherein the end effector frame includes a distal anvil support portion and an insert configured to receive a staple cartridge, wherein the distal anvil support portion includes a third alignment feature, wherein the insert includes first and second insert alignment features, wherein the fastener is configured to couple first and second alignment features of first and second portions with the first insert alignment feature of the insert, the frame further comprising a second fastener configured to coupled third alignment feature of distal anvil support portion with the first insert alignment feature of the insert.

Example 21

A frame of a curved surgical stapler comprising: (a) a shaft frame; (b) an end effector frame extending distally from the shaft frame, wherein the end effector frame includes: (i) a first portion that includes a first curvilinear portion and a first alignment feature, and (c) a fastener configured to couple the first and second alignment features of the first and second end effector frame portions together.

Example 22

The frame of Example 21, wherein the end effector frame further comprises a second portion that includes a second curvilinear portion a second alignment feature.

Example 23

The frame of any one or more of Examples 21 through 22, wherein the first portion is formed using metal injection molding, 3-D printing or stamping.

Example 24

The frame of any one or more of Examples 21 through 23, wherein the first portion is cut from a planar sheet of the material and subsequently bent to form the first portion.

Example 25

The frame of any one or more of Examples 21 through 24, wherein the first portion includes aligning lines configured to aid in bending the first portion along the aligning lines.

Example 26

The frame of any one or more of Examples 21 and Examples 23 through 25, wherein the first portion includes a second curvilinear portion of the end effector, a connecting portion extending distally from the first and second curvilinear portions of the end effector, and a distal anvil support portion extending distally from the connecting portion.

Example 27

The frame of Example 26, wherein first and second distal ends of the connecting portion are welded to the distal anvil support portion using at least one weld.

Example 28

The frame of any one or more of Examples 21 through 27, further comprising a third portion separate from either of the first or second portions, wherein the third portion includes a third alignment feature configured to align with the first and second alignment features of the first and second portions.

Example 29

The frame of Example 28, wherein the first, second, and third portions are aligned together using the first, second, and third alignment features.

Example 30

The frame of Examples 21 through 25 and Examples 27 through 29, wherein the first portion includes a first connecting portion extending distally from the first curvilinear portion, and a first distal anvil support portion extending distally from the first connecting portion, wherein the second portion includes a second curvilinear portion, a second connecting portion extending distally from the second curvilinear portion, and a second distal anvil support portion extending distally from the second connecting portion.

Example 31

The frame of any one or more of Examples 21 through 30, wherein the first and second portions are completely separate from each other prior to coupling first and second portions together.

Example 32

The frame of any one or more of Examples 21 through 25 and Examples 27 through 31, wherein the second portion includes a second curvilinear portion, wherein the first and second alignment features of the first and second portions are located between the first and second portions and not visible along an outer surface of the frame once the first and second portions are coupled together.

Example 33

The frame of any one or more of Examples 21 through 32, wherein the alignment feature of the first portion includes at least one projection or at least one recess, wherein the alignment feature of the second portion includes the other of the projection or the recess.

Example 34

The frame of any one or more of Examples 21 through 33, wherein the end effector frame includes first and second recessed portions, wherein each of the first and second recessed portions each include at least one coupling feature configured to couple the end effector frame to the curved surgical stapler.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

The entire disclosures of: U.S. Pat. No. 5,403,312, entitled "Electrosurgical Hemostatic Device," which issued on Apr. 4, 1995; U.S. Pat. No. 7,000,818, entitled "Surgical Stapling Instrument having Separate Distinct Closing and Firing Systems," which issued on Feb. 21, 2006; U.S. Pat. No. 7,422,139, entitled "Motor-Driven Surgical Cutting and Fastening Instrument with Tactile Position Feedback," which issued on Sep. 9, 2008; U.S. Pat. No. 7,464,849, entitled "Electro-Mechanical Surgical Instrument with Closure System and Anvil Alignment Components," which issued on Dec. 16, 2008; U.S. Pat. No. 7,670,334, entitled "Surgical Instrument Having An Articulating End Effector," which issued on Mar. 2, 2010; U.S. Pat. No. 7,753,245, entitled "Surgical Stapling Instruments," which issued on Jul. 13, 2010; U.S. Pat. No. 8,393,514, entitled "Selectively Orientable Implantable Fastener Cartridge," which issued on Mar. 12, 2013; U.S. Pat. No. 7,845,537, entitled "Surgical Instrument Having Recording Capabilities," which issued on Dec. 7, 2010; U.S. patent application Ser. No. 12/031,573, entitled "Surgical Cutting And Fastening Instrument Having RF Electrodes," filed Feb. 14, 2008, now abandoned; U.S. Pat. No. 7,980,443, entitled "End Effectors For A Surgical Cutting And Stapling Instrument," which issued on Jul. 19, 2011; U.S. Pat. No. 8,210,411 entitled "Motor-Driven Surgical Cutting Instrument," which issued on Jul. 3, 2012; U.S. Pat. No. 8,608,045, entitled "Powered Surgical Cutting And Stapling Apparatus With Manually Retractable Firing System," which issued on Dec. 17, 2013; U.S. Pat. No. 8,220,688, entitled "Motor-Driven Surgical Cutting Instrument with Electric Actuator Directional Control Assembly," which issued on Jul. 17, 2012; U.S. Pat. No. 8,733,613, entitled "Staple Cartridge," which issued on May 27, 2014; U.S. Pat. No. 8,561,870, entitled "Surgical Stapling Instrument," which issued on Oct. 22, 2013; U.S. Pat. No. 9,072,535, entitled "Surgical Stapling Instruments With Rotatable Staple Deployment Arrangements," which issued on Jul. 7, 2015; U.S. Pat. No. 9,101,358, entitled "Articulatable Surgical Instrument Comprising A Firing Drive," which issued on Aug. 11, 2015; U.S. Pat. No. 9,345,481, entitled "Staple Cartridge Tissue Thickness Sensor System," which issued on May 24, 2016; U.S. Patent Application Publication No. 2014/0263552, entitled "Staple Cartridge Tissue Thickness Sensor System," published on Sep. 18, 2014, now abandoned; U.S. Patent Application Publication No. 2007/0175955, entitled "Surgical Cutting And Fastening Instrument With Closure Trigger Locking Mechanism," published on Jan. 31, 2006, now abandoned; and U.S. Pat. No. 8,308,040, entitled "Surgical Stapling Instrument With An Articulatable End Effector," issued on Nov. 12, 2012, are hereby incorporated by reference herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a frame of a curved surgical stapler comprising:
   (a) manufacturing a first portion of the frame of the curved surgical stapler, wherein the first portion includes a first curvilinear portion of an end effector and a first alignment feature;
   (b) manufacturing a second portion of the frame of the curved surgical stapler separate from the first portion, wherein the second portion includes a second curvilinear portion and a second alignment feature;
   (c) manufacturing a third portion of the frame of the curved surgical stapler separate from either of the first or second portions, wherein the third portion includes a C-shaped track;
   (d) aligning the first portion with the second portion by aligning the first and second alignment features of the first and second portions of the curved surgical stapler; and
   (e) coupling the first, second, and third portions of the frame of the curved surgical stapler together which were formed separately so that the C-shaped track extends along a plane that transversely intersects a longitudinal axis defined by the frame.

2. The method of claim 1, wherein manufacturing the first and second portions further comprises metal injection molding, 3-D printing or stamping the first and second portions.

3. The method of claim 1, wherein the third portion includes a third alignment feature configured to align with the first and second alignment features of the first and second portions.

4. The method of claim 3, wherein aligning the first portion with the second portion further comprises aligning the first, second, and third portions together using the first, second, and third alignment features.

5. The method of claim 4, wherein coupling the first and second portions together further comprises inserting a fastener into the first, second, and third alignment features of the first, second, and third portions.

6. The method of claim 1, wherein the first portion includes a first connecting portion extending distally from the first curvilinear portion, and a first distal anvil support portion extending distally from the first connecting portion, wherein the second portion includes a second curvilinear portion, a second connecting portion extending distally from the second curvilinear portion, and a second distal anvil support portion extending distally from the second connecting portion.

7. The method of claim 1, wherein the first and second portions of the frame are completely separate from each other prior to coupling first and second portions together.

8. The method of claim 1, wherein the first and second alignment features of the first and second portions are located between the first and second portions and not visible along an outer surface of the frame once the first and second portions are coupled together.

9. The method of claim 1, wherein the first alignment feature of the first portion includes at least one projection or at least one recess, wherein the second alignment feature of the second portion includes the other of the projection or the recess, wherein aligning the first portion with the second portion comprises aligning the at least one projection with the at least one recess.

10. The method of claim 1, wherein aligning the first portion with the second portion causes the first curvilinear portion to extend parallel with the second curvilinear portion.

11. The method of claim 1, wherein the C-shaped track includes an enlarged portion configured to receive a distal portion of retaining pin of the curved surgical stapler.

12. The method of claim 1, wherein coupling the first, second, and third portions of the frame of the curved surgical stapler together further comprises coupling the first, second, and third portions of the frame of the curved surgical stapler together using a fastener.

13. A method of manufacturing a frame of a curved surgical stapler comprising:
(a) metal injection molding or 3-D printing an end effector frame of the curved surgical stapler, wherein the end effector frame includes a C-shaped track, a first curvilinear portion, and a first alignment feature, wherein the C-shaped track extends along a plane that transversely intersects a longitudinal axis defined by the frame;
(b) manufacturing a first handle frame of the curved surgical stapler separate from the end effector frame, wherein the first handle frame includes a first shaft
(c) aligning the end effector frame with the first handle frame by aligning the first alignment feature with the first shaft alignment feature of the curved surgical stapler; and
(d) coupling the end effector frame and the first handle frame of the curved surgical stapler together.

14. The method of claim 11, further comprising:
(a) stamping a second handle frame including a second shaft alignment feature;
(b) coupling the end effector frame to the second handle frame by coupling a second alignment feature of the end effector frame with the second shaft alignment feature using at least one fastener.

15. The method of claim 14, wherein the first handle frame comprises a first elongate shaft portion and a first handle portion, wherein the second handle frame comprises a second elongate shaft portion and a second handle portion.

16. The method of claim 13, wherein after metal injection molding or 3-D printing the end effector frame, machining the end effector frame to include a distal anvil support portion into the end effector frame.

17. A method of manufacturing a frame of a curved surgical stapler comprising:
(a) stamping a first portion of the frame of the curved surgical stapler, wherein the first portion includes a first alignment feature;
(b) bending the first portion to form first and second curvilinear portions of an end effector;
(c) manufacturing a second portion of the frame of the curved surgical stapler separate from the first portion, wherein the second portion includes a second alignment feature;
(d) manufacturing a third portion of the frame of the curved surgical stapler separate from either of the first or second portions, wherein the third portion includes a C-shaped track;
(e) aligning the first portion with the second portion by aligning the first and second alignment features of the first and second portions of the curved surgical stapler; and
(f) coupling the first, second, and third portions of the frame of the curved surgical stapler together so that the C-shaped track extends along a plane that transversely intersects a longitudinal axis defined by the frame.

18. The method of claim 17, wherein stamping the first portion further comprises cutting the first portion from a planar sheet of material and subsequently bending the first portion.

19. The method of claim 18, further comprising:
imparting aligning lines in the first portion prior to bending the first portion along the aligning lines.

20. The method of claim 17, wherein the first portion includes a second curvilinear portion of the end effector, a connecting portion extending distally from the first and second curvilinear portions of the end effector, and a distal anvil support portion extending distally from the connecting portion, wherein bending the first portion further comprises bending the first portion to form the first and second curvilinear portions of the end effector, the connecting portion, and the distal anvil support portion.

* * * * *